(12) United States Patent
Fischer et al.

(10) Patent No.: US 8,048,026 B2
(45) Date of Patent: Nov. 1, 2011

(54) DEFLECTABLE CATHETER STEERING AND LOCKING SYSTEM

(75) Inventors: Brian Fischer, Minneapolis, MN (US); Bradley Charles Knippel, Lino Lakes, MN (US)

(73) Assignee: Greatbatch Ltd., Clarence, NY (US)

( * ) Notice: Subject to any disclaimer, the term of this patent is extended or adjusted under 35 U.S.C. 154(b) by 45 days.

(21) Appl. No.: 12/714,122

(22) Filed: Feb. 26, 2010

(65) Prior Publication Data

US 2010/0160858 A1 Jun. 24, 2010

Related U.S. Application Data

(63) Continuation of application No. 12/364,391, filed on Feb. 2, 2009, now Pat. No. 7,678,074, which is a continuation of application No. 11/122,779, filed on May 5, 2005, now Pat. No. 7,497,853.

(51) Int. Cl.
*A61M 31/00* (2006.01)
*A61M 37/00* (2006.01)

(52) U.S. Cl. .................................. 604/95.04

(58) Field of Classification Search ............... 604/95.01, 604/95.04, 95.05, 510, 523–528, 530
See application file for complete search history.

(56) References Cited

U.S. PATENT DOCUMENTS

| | | |
|---|---|---|
| 4,586,923 A | 5/1986 | Gould et al. |
| 5,030,204 A | 7/1991 | Badger et al. |
| 5,190,050 A | 3/1993 | Nitzsche |
| 5,275,151 A | 1/1994 | Shockey et al. |
| 5,327,905 A | 7/1994 | Avitall |
| 5,354,297 A | 10/1994 | Avitall |
| 5,358,479 A | 10/1994 | Wilson |
| 5,441,483 A | 8/1995 | Avitall |
| 5,462,527 A | 10/1995 | Stevens-Wright et al. |
| 5,487,757 A | 1/1996 | Truckai et al. |
| 5,599,305 A | 2/1997 | Hermann et al. |
| 5,642,736 A | 7/1997 | Avitall |
| 5,666,970 A | 9/1997 | Smith |
| 5,741,320 A | 4/1998 | Thornton et al. |
| 5,861,024 A | 1/1999 | Rashidi |

(Continued)

FOREIGN PATENT DOCUMENTS

| | | |
|---|---|---|
| WO | WO-96/34650 A1 | 11/1996 |
| WO | WO-98/33429 A2 | 8/1998 |

OTHER PUBLICATIONS

"U.S. Appl. No. 12/364,391 Notice of Allowance Mailed Oct. 13, 2009", 10 pgs.

(Continued)

*Primary Examiner* — Nicholas Lucchesi
*Assistant Examiner* — Nathan R Price
(74) *Attorney, Agent, or Firm* — Michael F. Scalise; Schwegman, Lundberg & Woessner, P.A.

(57) ABSTRACT

A deflectable catheter includes a catheter shaft having a deflectable distal tip. A support member is coupled around a proximal portion of the catheter shaft, and the support member includes a first brake portion extending along at least a portion of the support member. A handle is coupled around the support member. The deflectable catheter includes a carriage moveably coupled along the handle, and the carriage includes a second brake portion sized and shaped to engage with at least a portion of the first brake portion. A flexible element is coupled between the deflectable distal tip and the carriage. A biasing device is adapted to bias the second brake portion into engagement with the first brake portion.

21 Claims, 13 Drawing Sheets

U.S. PATENT DOCUMENTS

| | | | |
|---|---|---|---|
| 5,944,727 | A | 8/1999 | Ahari et al. |
| 6,251,092 | B1 * | 6/2001 | Qin et al. .................. 604/95.01 |
| 6,648,875 | B2 | 11/2003 | Simpson et al. |
| 6,652,506 | B2 | 11/2003 | Bowe et al. |
| 7,497,853 | B2 | 3/2009 | Fischer et al. |
| 7,678,074 | B2 | 3/2010 | Fischer et al. |
| 2002/0019591 | A1 | 2/2002 | Bon |
| 2003/0050598 | A1 | 3/2003 | Hayzelden |
| 2003/0109778 | A1 | 6/2003 | Rashidi |
| 2003/0149422 | A1 | 8/2003 | Muller |
| 2003/0163085 | A1 | 8/2003 | Tanner et al. |
| 2005/0065467 | A1 | 3/2005 | Pudelko et al. |
| 2006/0264819 | A1 | 11/2006 | Fischer et al. |
| 2009/0137953 | A1 | 5/2009 | Fischer et al. |

OTHER PUBLICATIONS

"U.S. Appl. No. 11/122,779, Examiner Interview Summary mailed Aug. 19, 2008", 7 pgs.

"U.S. Appl. No. 11/122,779, Non-Final Office Action mailed May 14, 2008", 23 pgs.

"U.S. Appl. No. 11/122,779, Notice of Allowance mailed Nov. 26, 2008", 8 pgs.

"U.S. Appl. No. 11/122,779, PTO Response to Rule 312 Amendment mailed Jan. 14, 2009", 2 pgs.

"U.S. Appl. No. 11/122,779, Response filed Aug. 14, 2008 to Non Final Office Action mailed May 14, 2008", 18 pgs.

"European Application Serial No. 06252399.8, Office Action mailed on Jan. 29, 2009", 4 pgs.

"European Application Serial No. 06252399.8, Response filed May 27, 2009 to Office Action mailed Jan. 29, 2009", 7 pgs.

"European Application Serial No. 06252399.8, Response filed Oct. 14, 2008 to EP Search Report mailed Feb. 11, 2008", 21 pgs.

"European Search Report for EP 06 25 2399, mailed Feb. 11, 2008", 6 pages.

* cited by examiner

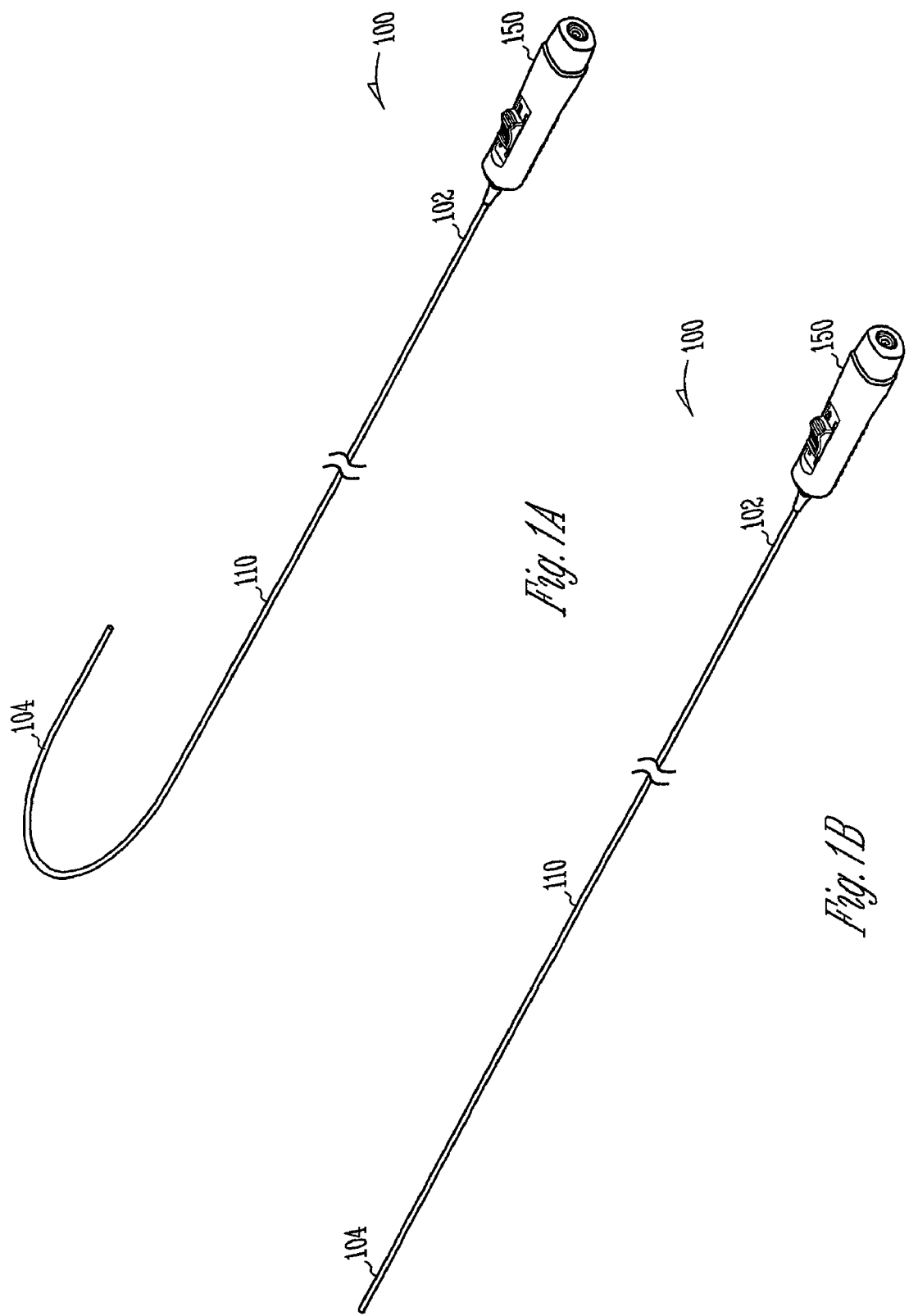

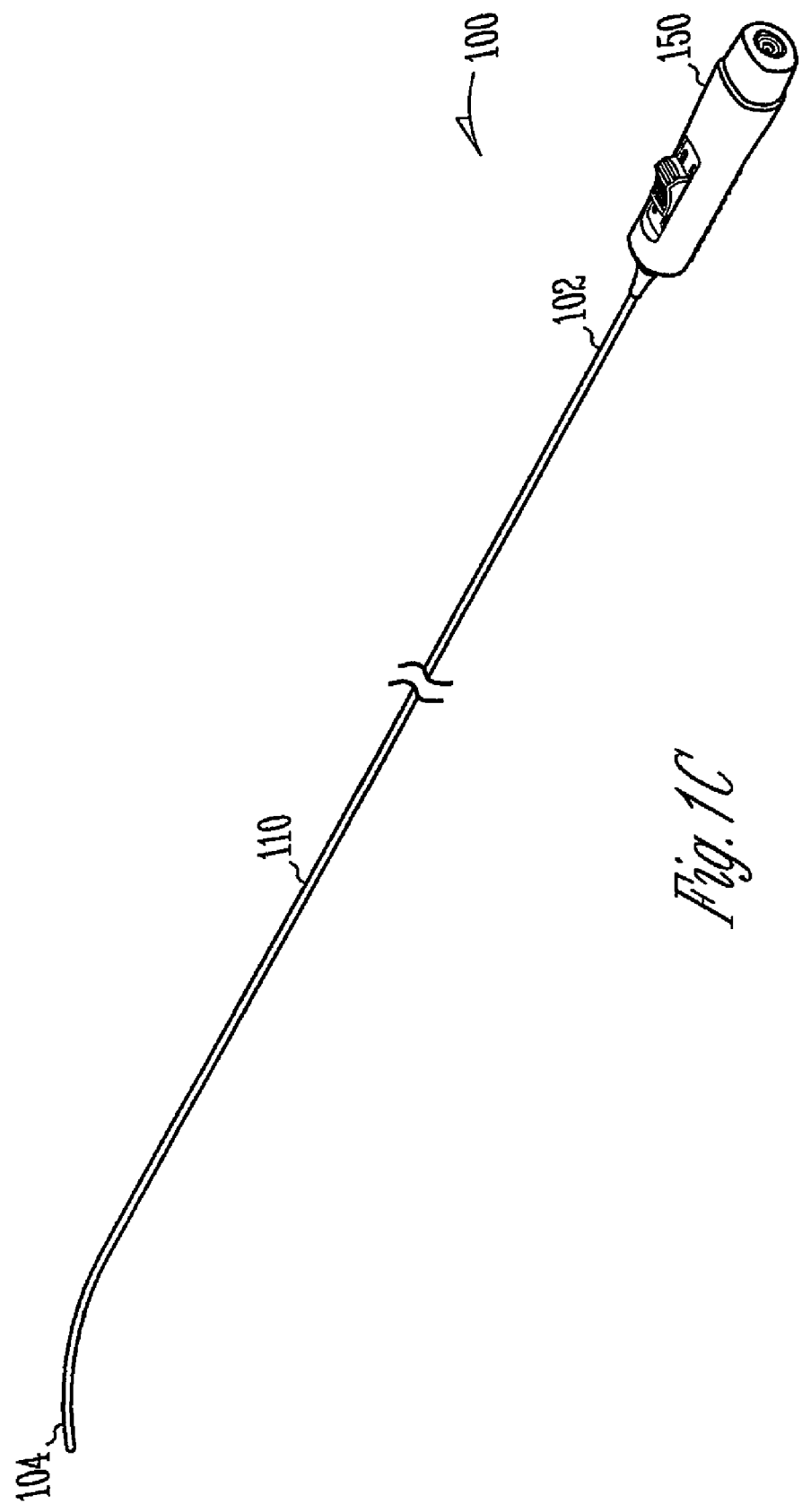

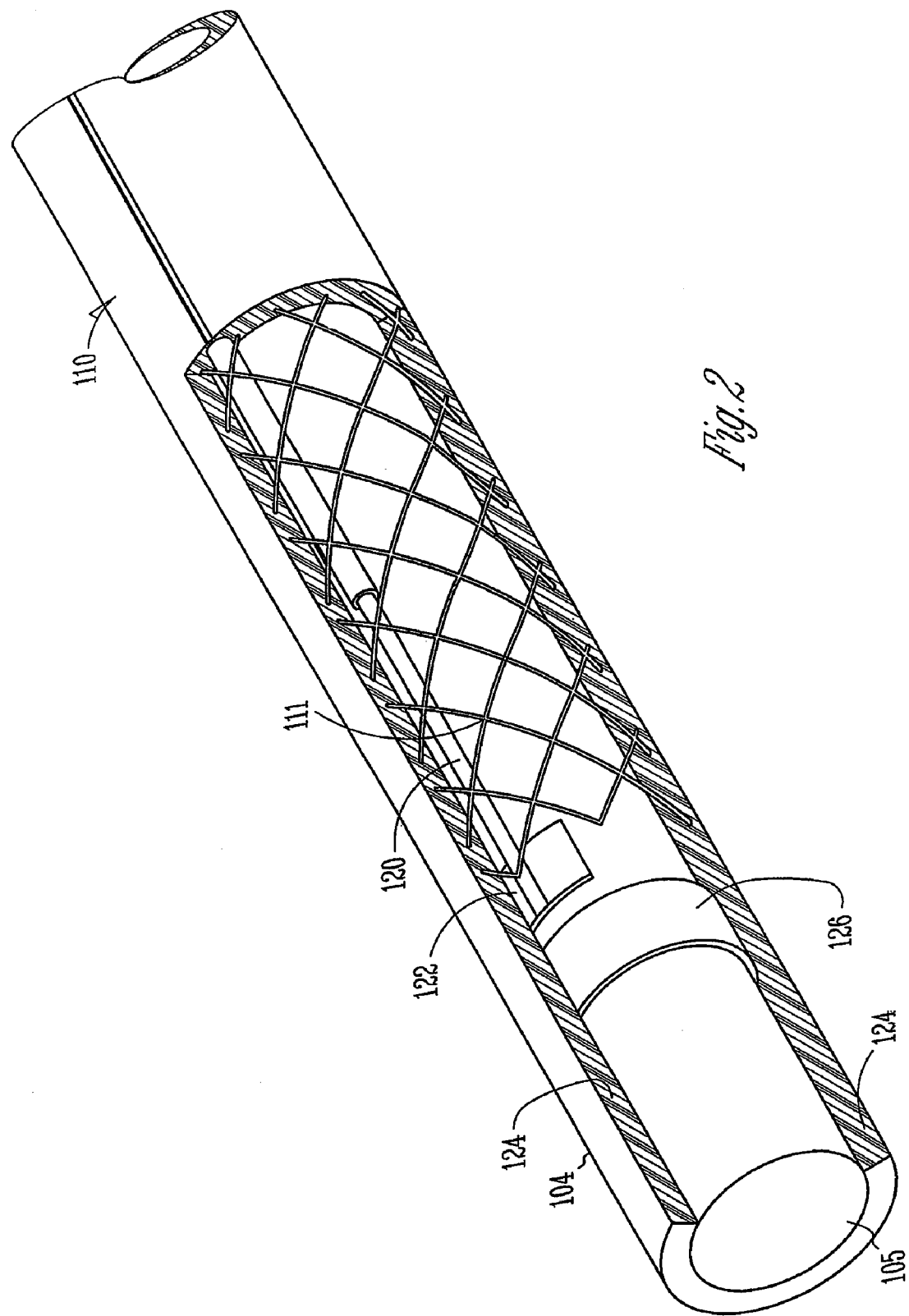

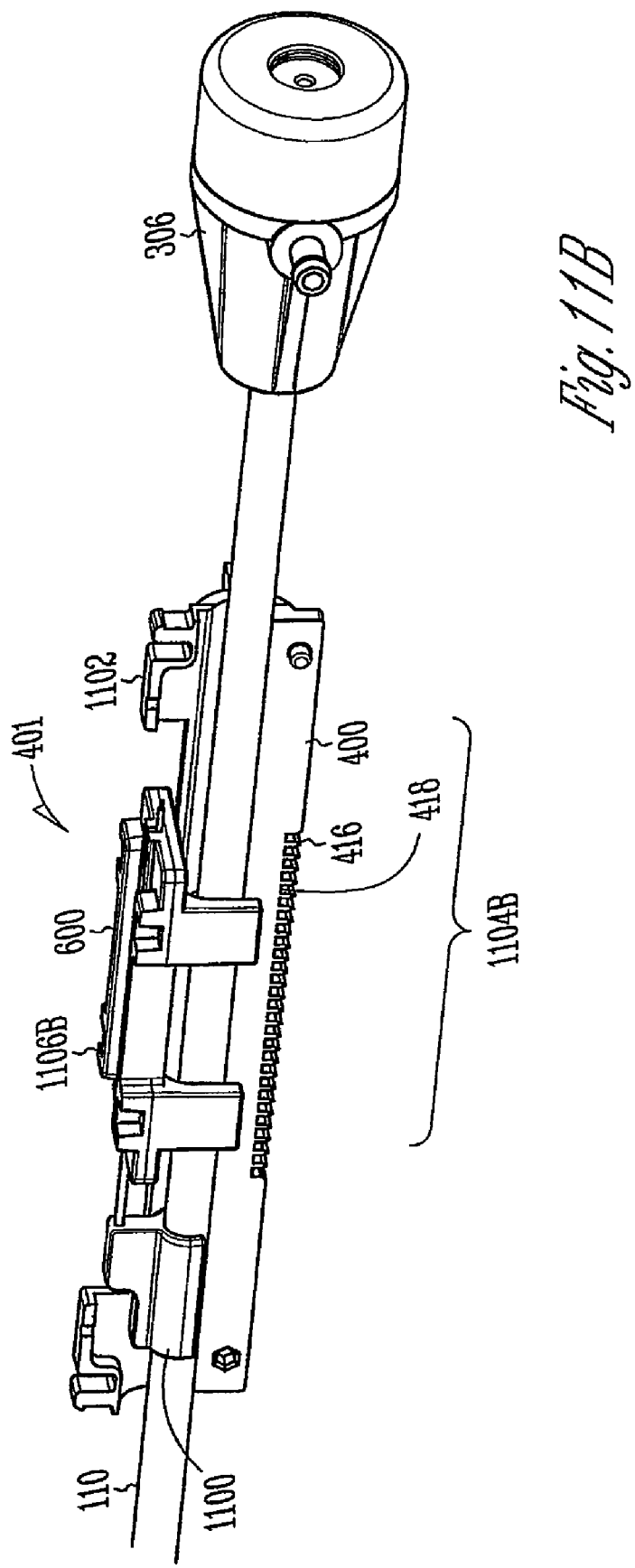

1200

1202
COUPLE A FLEXIBLE ELEMENT TO A DEFLECTABLE DISTAL TIP OF A CATHETER SHAFT

1204
COUPLE A SUPPORT MEMBER AROUND A PROXIMAL PORTION OF THE CATHETER SHAFT, WHEREIN THE SUPPORT MEMBER INCLUDES A FIRST BRAKE PORTION EXTENDING ALONG AT LEAST A PORTION OF THE SUPPORT MEMBER

1206
COUPLE A HANDLE TO THE SUPPORT MEMBER

1208
MOVEABLY COUPLE A CARRIAGE ASSEMBLY WITH THE HANDLE, WHEREIN THE CARRIAGE ASSEMBLY INCLUDES A CARRIAGE HAVING A SECOND BRAKE PORTION SHAPED TO ENGAGE WITH AT LEAST A PORTION OF THE RACK

1210
COUPLE THE FLEXIBLE ELEMENT TO THE CARRIAGE ASSEMBLY

1212
COUPLE A BIASING DEVICE BETWEEN THE CARRIAGE ASSEMBLY AND THE HANDLE, WHEREIN THE BIASING DEVICE IS MOVEABLY COUPLED ALONG THE HANDLE, AND THE BIASING DEVICE IS ADAPTED TO BIAS THE SECOND BRAKE PORTION INTO ENGAGEMENT WITH THE FIRST BRAKE PORTION

*Fig. 12*

DEFLECTABLE CATHETER STEERING AND LOCKING SYSTEM

CROSS-REFERENCE TO RELATED APPLICATION

This application is a continuation of U.S. application Ser. No. 12/364,391, which is a continuation of U.S. Pat. No. 7,497,853, each of which are incorporated herein by reference.

TECHNICAL FIELD

Deflectable catheters and in particular to steering and locking systems for retaining a desired orientation of a deflectable catheter distal tip.

BACKGROUND

Many current deflectable catheters include some form of locking device configured to retain a deflected portion of the catheter in the deflected orientation. In some examples, locking mechanisms and deflection mechanisms are separate from each other, thereby requiring dual controls and complicating use and manufacture of the catheter. For instance, the grip on the handle must be repeatedly readjusted to switch between actuating the locking mechanism and the deflection mechanism. Further, space in the handle must be set aside for separate locking and deflection mechanisms, thereby requiring tightly packed and complex handles or larger handles to accommodate the mechanisms.

Other examples of catheters include ratcheting teeth that prevent movement of a deflection control actuator in one direction while permitting movement of the actuator in another direction and corresponding continued deflection of the catheter. Ratcheting engagement of the actuator with the handle permits undesired deflection of the catheter, for example, where the catheter engages against vasculature during longitudinal movement of the catheter.

In still other examples, pull wires extend from the deflectable tip of a catheter shaft to the deflection control actuator, and the pull wires are not constrained from lateral movement within the handle. The pull wire may only be tensioned in one direction in this configuration thereby only allowing deflection in a single direction. Compression of the pull wire in another direction will buckle the wire and thereby substantially prevent active deflection of the catheter with the deflection control actuator. Straightening of the catheter in a direction opposed to that granted by tensioning the pull wire is thereby accomplished with the natural elasticity of the catheter distal tip. The deflected shaft exerts a passive pulling force on the pull wire that straightens the catheter without active control through the deflection control actuator. Further, the elasticity of the catheter only straightens the catheter and does not deflect the catheter in an opposed direction.

Additionally, in yet other examples, deflectable catheters include locking surfaces formed with the handle that substantially prevent adjustment of a range of travel for the deflection control actuator. For instance, the locking surfaces are formed along an interior surface of the handle. Changing the range of travel for the actuator requires redesigning the handle with a differently positioned locking surface. Multiple handle designs are therefore needed to accommodate desired ranges of travel for different catheter sizes, ranges of deflection and the like.

What is needed is a deflectable catheter that overcomes the shortcomings of previous designs. What is further needed is an easy to use deflectable catheter with locking and deflection functions that is not limited to passive deflection to straighten the catheter.

SUMMARY

A deflectable catheter including a catheter shaft having a deflectable distal tip. A support member is coupled around a proximal portion of the catheter shaft, and the support member includes a first brake portion extending along at least a portion of the support member. The deflectable catheter further includes a handle coupled around the support member. A carriage is moveably coupled along the handle, and the carriage includes a second brake portion sized and shaped to engage with at least a portion of the first brake portion and substantially prevent movement of the carriage relative to the handle. A flexible element is coupled between the deflectable distal tip and the carriage. A biasing device is coupled between the carriage and the handle, and the biasing device is adapted to bias the second brake portion into engagement with the first brake portion. In one option, the first brake portion is a rack and the second brake portion is at least one projection sized and shaped to engage with the rack.

Several options for the deflectable catheter follow. In one option, the catheter shaft includes a flexible element guide and the flexible element extends outside of the catheter shaft at the flexible element guide. The support member includes, in another option, a proximal stop proximal to the rack. Optionally, the carriage has a range of travel between the flexible element guide and the proximal stop, and the support member is coupled around a predetermined location of the catheter shaft to define the range of travel.

In another option, the carriage includes an actuator adapted to move at least a portion of the carriage between a first position where the at least one projection is engaged with the rack and a second position where the at least one projection is disengaged with the rack. In yet another option, the deflectable catheter includes a carriage guide slidably coupled with the carriage, and the carriage guide is sized and shaped to permit lateral movement of a portion of the carriage and substantially prevent lateral movement of a second portion of the carriage. The carriage guide is sized and shaped to permit longitudinal movement of the carriage along the handle.

A method for making a deflectable catheter includes coupling a flexible element to a deflectable distal tip of a catheter shaft. A support member is coupled around a proximal portion of the catheter shaft, and the support member includes a first brake portion extending along at least a portion of the support member. A handle is coupled around the support member. In one option, the handle is coupled around a hemostasis valve, and the hemostasis valve is in communication with a delivery lumen of the catheter shaft. The method further includes moveably coupling a carriage assembly with the handle. The carriage assembly includes a carriage having second brake portion sized and shaped to engage with at least a portion of the first brake portion. A flexible element is coupled with the carriage assembly. A biasing device is coupled between the carriage assembly and the handle and moveably coupled along the handle. The biasing device is adapted to bias the second brake portion into engagement with the first brake portion. Optionally, the method includes coupling an actuator with the carriage. The actuator is adapted to move the carriage between a first position where the second brake portion is engaged with the first brake portion and a second position where the second brake portion is disengaged with the first brake portion.

Several options for the method follow. In one option, a retainer is slidably coupled with the carriage, and the flexible element is coupled with the retainer. The retainer is sized and shaped to move with the carriage longitudinally along the handle, and the retainer is sized and shaped to remain substantially laterally static relative to the flexible element, for instance when the carriage is moved laterally. Optionally, the method includes slidably coupling a carriage guide with the carriage assembly, and the carriage guide is sized and shaped to permit lateral movement of the carriage relative to the flexible element and substantially prevent lateral movement of the retainer. The carriage guide is sized and shaped to permit movement of the carriage assembly longitudinally along the handle.

The above described deflectable catheter provides a steering and locking system capable of locking the deflectable distal tip in a desired deflected position. The carriage and retainer cooperate with the support member to longitudinally move the flexible element to deflect the distal tip and lock the distal tip in a desired deflected position. The steering and locking system substantially prevents movement of the carriage proximally or distally, thereby substantially preventing further undesired deflection of the catheter or straightening when the carriage is in the locked position. Optionally, the steering and locking system automatically locks the catheter in a desired orientation by releasing the actuator. In one option, the carriage includes the second brake portion having, for instance, multiple projections that provide a strong locking force between the carriage and the first brake portion (e.g., rack, high friction surface and the like) of the support member to securely retain the distal tip of the catheter in a deflected orientation.

As described above, the carriage assembly including the carriage and retainer are operated to deflect the distal tip and lock the distal tip in a desired deflected position. The carriage assembly thereby consolidates the deflection system with the locking system into the single steering and locking system to simplify use of the catheter. In another option, a single actuator is used to control both the deflection and locking of the deflectable catheter. Additional controls and the like are unnecessary. Further, combining the deflection and locking features decreases labor and manufacturing costs. Moreover, in another option, the catheter handle includes a hemostasis valve and/or flush port therein to further simplify use of the deflectable catheter.

Additionally, the support member provides a brake portion for locking the carriage in place and is a structural support to the catheter shaft during deflection and traversing of the vasculature. Moreover, the support member is coupled along the catheter shaft at a predetermined location to provide a range of travel for the carriage, and thereby a range of deflection of the distal tip. The space between the proximal stop of the support member and the flexible element guide along the catheter shaft defines the range of travel and corresponding range of deflection for the distal tip. Coupling the support member distally toward the flexible element guide provides a short range of travel (e.g., for thin walled catheters). Coupling the support member proximally away from the flexible element guide provides a longer range of travel (e.g., for thicker catheters, greater deflection ranges, and the like). Further, coupling the support member at the predetermined location also establishes a neutral position for the carriage where the deflectable distal tip assumes an undeflected orientation. The support member is coupled along the catheter body at a variety of locations to define a corresponding variety of ranges of travel. In yet another option, the support member is coupled with a standard handle sized and shaped to receive the support member. A single handle is thereby used with the same support member no matter what the range of travel is of the carriage assembly thereby decreasing labor and manufacturing costs.

Further, the retainer and tube assembly substantially prevent buckling of the flexible element thereby allowing tension and compression loading of the flexible element. Because the flexible element is constrained from moving laterally between the retainer and the deflectable distal tip the element is loadable in tension and compression to provide bi-directional deflection of the distal tip. In another option, loading the flexible element in compression permits active straightening of the deflected catheter thereby providing active control for deflection and straightening with the carriage assembly (i.e., the natural catheter elasticity does not unpredictably control straightening of the distal tip). The carriage guide, in yet another option, facilitates longitudinal movement of the carriage and the retainer while holding the retainer in a substantially laterally static position with respect to the flexible element. The carriage guide thereby ensures the retainer cooperates with the tube assembly to keep the flexible element laterally static, while permitting longitudinal movement of the carriage assembly for deflection of the distal tip. Additionally, the carriage guide permits lateral movement of the carriage to engage and disengage the second brake portion of the carriage with the first brake portion of the support member.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1A is a perspective view of one example of a deflectable catheter in a first deflected orientation.

FIG. 1B is a perspective view of the deflectable catheter in a neutral orientation.

FIG. 1C is a perspective view of the deflectable catheter in a second deflected orientation.

FIG. 2 is a partial sectional view of one example of the deflectable distal tip.

FIG. 11B is a perspective view of still another example of the steering and locking system including the carriage assembly having a second range of travel between the flexible element guide and the proximal stop.

FIG. 12 is a block diagram showing one example of a method for making a deflectable catheter.

DESCRIPTION OF THE EMBODIMENTS

Figure 3:
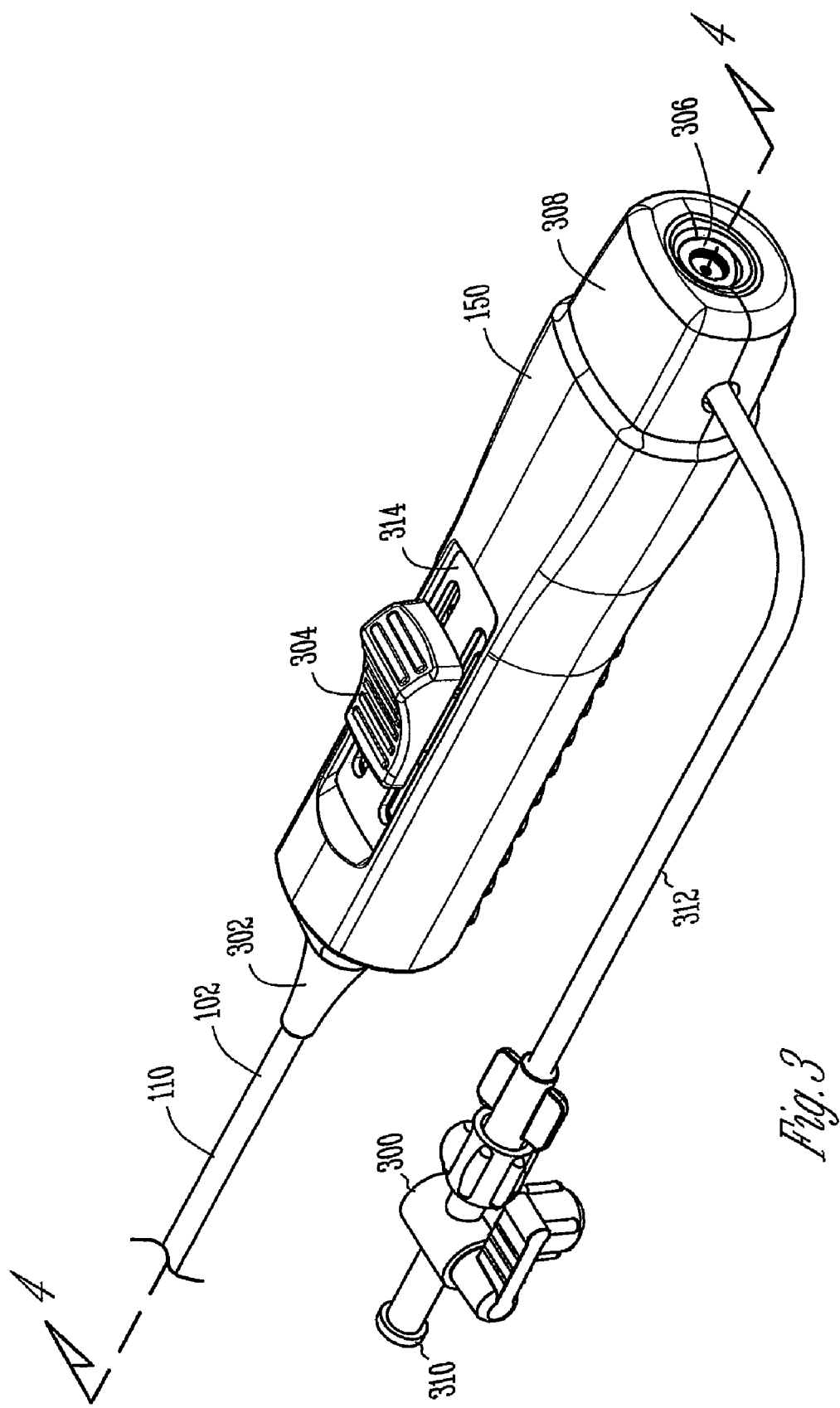
FIG. 3 is a perspective view of one example of the catheter handle assembly including a flush port.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

FIGS. 1A, 1B and 1C illustrate a deflectable catheter assembly 100, where FIG. 1A illustrates the deflectable catheter assembly 100 in one articulated position, and FIG. 1C illustrates the catheter assembly 100 in another articulated orientation. FIG. 1B illustrates the deflectable catheter assembly 100 in an unarticulated neutral position. The deflectable catheter assembly 100 includes a catheter body 110 and a handle assembly 150 that houses a steering and locking mechanism for deflection of the catheter body 110. The handle assembly 150 allows for the selectable deflection of a distal end of the catheter body 110 into any number of disparate orientations, as further described below.

The catheter body 110 comprises an elongate tubular construction that is flexible yet substantially non-compressible along its length. The deflectable catheter body 110 extends from a proximal end 102 to a deflectable distal tip 104, where the deflectable distal tip 104 is adapted to be disposed within a patient. At the proximal end 102, the physician controls the deflection of the deflectable catheter body 110 with the handle assembly 150 containing the steering and locking mechanism and a flexible element, such as a push-pull wire, as further described below. The deflectable distal tip 104 is deflected to traverse various branch vessels with the catheter assembly 100 (FIG. 1A and 1C).

FIG. 2 illustrates a partial cut-away view of the deflectable distal tip 104 shown in FIGS. 1A, B, C. The catheter body 110 includes a delivery lumen 105, in one option. The delivery lumen 105 extends through the catheter body 110 between the proximal end 102 and the deflectable distal tip 104. The delivery lumen 105 is sized and shaped to receive, for example, instruments, fluids, media and the like. A flexible element 120, such as a push-pull wire, extends through the catheter body 110 and into the deflectable distal tip 104. The flexible element 120, in another option, extends through the catheter sidewall 124 surrounding the delivery lumen 105. The deflectable distal tip 104 includes an anchor 122 coupled with the flexible element 120. The anchor 122 is coupled with the catheter body 110 at the deflectable distal tip 104 and transmits pushing and pulling forces from the flexible element 120 to the deflectable distal tip to cause deflection of the distal tip. In one option, the anchor 122 is encapsulated within the catheter sidewall 124 with an encapsulant, such as a plastic. Optionally, the encapsulant includes, but is not limited to PEBAX a registered trademark of the Atofina Corporation. It should be noted that the flexible element 120 can be secured to the deflectable distal tip 104 of the catheter body 110 by other means such as coupling with a marker band 126. The marker band 126 is constructed with a material that is visible with an imaging procedure, such as fluoroscopy. In another option, the flexible element 120 is coupled to the marker band 126 and/or anchor 122 by crimping, welding, soldering, brazing, interference fitting and the like. In one option, the catheter body 110 includes a stiffening member embedded therein, such as a braided stainless steel member 111. The stiffening member facilitates rotation of the deflectable distal tip 104 from the proximal end 102, and also assists in preventing the catheter body 110 from collapsing.

FIG. 3 shows one example of the handle assembly 150 with a flush port 300 coupled to the assembly 150. The handle assembly 150 is coupled with the proximal end 102 of the catheter body 110. In one option, the handle assembly 150 includes a strain relief fitting 302 surrounding at least a portion of the proximal end 102 and coupled with the handle assembly 150. The strain relief fitting 302 extends toward the deflectable distal tip 104 to provide support to the proximal end 102 of the catheter body 110. The strain relief fitting 302, in another option, has a predetermined stiffness that provides support to the proximal end 102 to minimize kinking of the catheter body 110 adjacent to the handle assembly 150. In yet another option, the strain relief fitting 302 is constructed with plastics, metals and the like. For instance, the strain relief fitting 302 includes SANTOPRENE a registered trademark of Advanced Elastomer Systems, L.P. The handle assembly 150 and the components therein are constructed with, but not limited to, plastics, metals and the like. In one example, the handle assembly 150 is constructed with a composite such as a glass fiber filled polycarbonate. Optionally, the handle assembly 150 and its components are formed by molding, machining, extrusion, pultrusion and the like. In yet another option, the handle assembly 150 is formed with a plurality of processes (e.g., molding and machining).

As shown in FIG. 3, the handle assembly 150 includes an actuator 304, such as a slide. In another option, the actuator 304 includes, but is not limited to, a button, wheel, knob and the like. The actuator 304, in yet another option, is constructed with a plastic, such as polycarbonate. The actuator 304 is part of a steering and locking system (described below) and is operated to deflect the deflectable distal tip 104 (FIGS. 1A, B, C and 2). Optionally, the actuator 304 is moved proximally and distally along the handle assembly 150 (e.g., with thumb or finger pressure) to actively control deflection of the distal tip 104. As further described below, the actuator 304 is moveable laterally with respect to the handle assembly 150 (e.g., toward and away from the handle assembly) to lock the deflectable distal tip 104 in a desired orientation.

In another option, the handle assembly 150 includes an access point, such as a hemostasis valve 306. The hemostasis valve 306, optionally, is positioned at the proximal end 308 of the handle assembly 150 and provides access to the delivery lumen 105 (FIG. 2). The hemostasis valve 306 allows for insertion of instruments and devices having a variety of sizes into the delivery lumen 105. The hemostasis valve 306 substantially prevents blood loss out of the delivery lumen 105 and the entrance of air and other gases into the delivery lumen 105 during insertion and extraction of the instruments and devices. The hemostasis valve 306 is constructed with, but not limited to, plastics, metals and the like. In one example, the hemostasis valve 306 includes glass fiber filled nylon and has a flexible silicone membrane to permit passage of instruments and devices. In yet another option, the handle assembly 150 includes a luer fitting sized and shaped to couple with a variety of components (e.g., instruments and the like) that have a mating luer fitting.

In yet another option, the flush port assembly 300 is in communication with the delivery lumen 105 (FIG. 2) by a tube 312 coupled therebetween. The flush port assembly 300 includes a nozzle 310 sized and shaped to receive a fluid, for instance saline. Fluids are injected into the delivery lumen 105 through the flush port assembly 300. In one example, saline is injected through the flush port assembly 300 to flush air out of the delivery lumen 105. In another example, fluids, such as contrast media, medications and the like are injected through the flush port assembly 300 and fed down the delivery lumen 105 to a targeted area (e.g., within a vessel).

Figure 4:
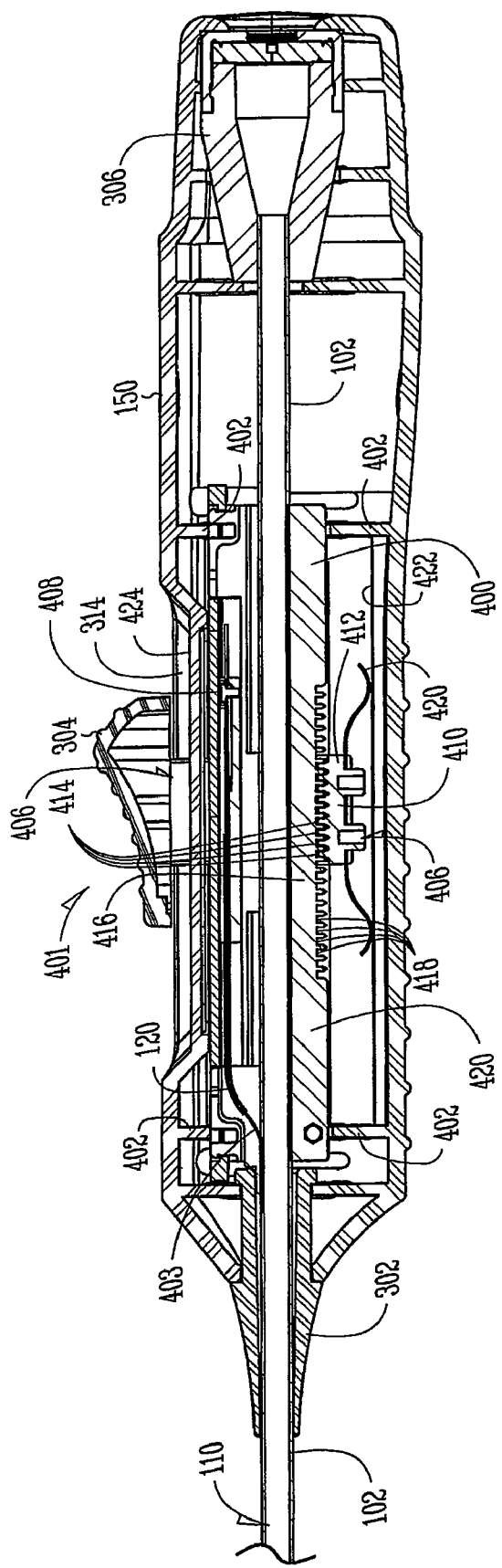
FIG. 4 is a cross section of the catheter handle assembly taken along line 4-4 of FIG. 3.

FIG. 4 is a cross sectional view of the handle assembly 150 taken along line 4-4 of FIG. 3 and showing a steering and locking system 401. The proximal end 102 of the catheter body 110 extends through at least a portion of the handle assembly 150. In one option, the proximal end 102 is in communication with the hemostasis valve 306 described above. As shown in FIG. 4, the proximal end 102 of the catheter body 110 is coupled with the handle assembly 150 by a support member 400, in another option. The support member 400 extends around at least a portion of the proximal end 102 and secures the catheter body 110 to the handle assembly 150. The proximal end 102 is held within the support member 400 and substantially constrained from moving laterally or longitudinally and the support member 400 thereby provides a strong structural coupling between the catheter body 110 and the handle assembly 150. Optionally, the support member 400 clamps around the proximal end 102 to secure the catheter body 110 to the handle assembly 150. In yet another option, adhesives, welds, fasteners and like are used to couple the catheter body 110 to the support member 400 and the handle assembly 150. The support member 400 is positioned near the center of the handle assembly 150 and retained therein by ribs 402 extending between the support member 400 and the handle assembly 150. The ribs 402, in still another option, extend around at least a portion of the support member 400. The ribs 402 extend into recesses (described below in FIG. 6), in an option, of the support member 400 to substantially prevent movement of the support member 400 and catheter body relative to the handle assembly 150. The ribs 402 and the support member 400 cooperate to align the proximal end 102 of the catheter body 110 with the hemostasis valve 306 and the strain relief fitting 302 (described above). The support member 400 is retained in the handle assembly 150, in still another option, with adhesives, welds, fasteners and the like. Optionally, the support member 400 is constructed with plastics, metals and the like. The support member 400 includes polycarbonate, in one example.

As described above, the flexible element 120 extends from the deflectable distal tip (FIG. 2) through the catheter body 110. As shown in FIG. 4, the flexible element 120 exits the catheter body 110 at a sidewall exit 403 of the proximal end 102 and is coupled with a carriage assembly 406 moveably coupled along the handle assembly 150. The flexible element 120 is coupled with the carriage assembly 406 with a retaining pin 408 (e.g., a stainless steel retaining pin), in one option. In another option, the flexible element 120 is coupled with the carriage assembly 406 with, but not limited to, welds, set screws, clamps, adhesives and the like. Moving the carriage assembly 406 of the steering and locking system 401 longitudinally along the handle assembly 150 moves the flexible element 120 coupled with the assembly 406. Movement of the flexible element 120 is transmitted to the deflectable distal tip 104 (FIG. 2) and deflects the distal tip 104 into a variety of orientations, including for instance the orientations shown in FIGS. 1A, C. In yet another option, the movement of the carriage assembly 406 and corresponding movement of the flexible element 120 straightens the deflectable distal tip 104 from a deflected orientation (FIGS. 1A, C) into a substantially straight neutral position, as shown in FIG. 1B.

Figure 5:
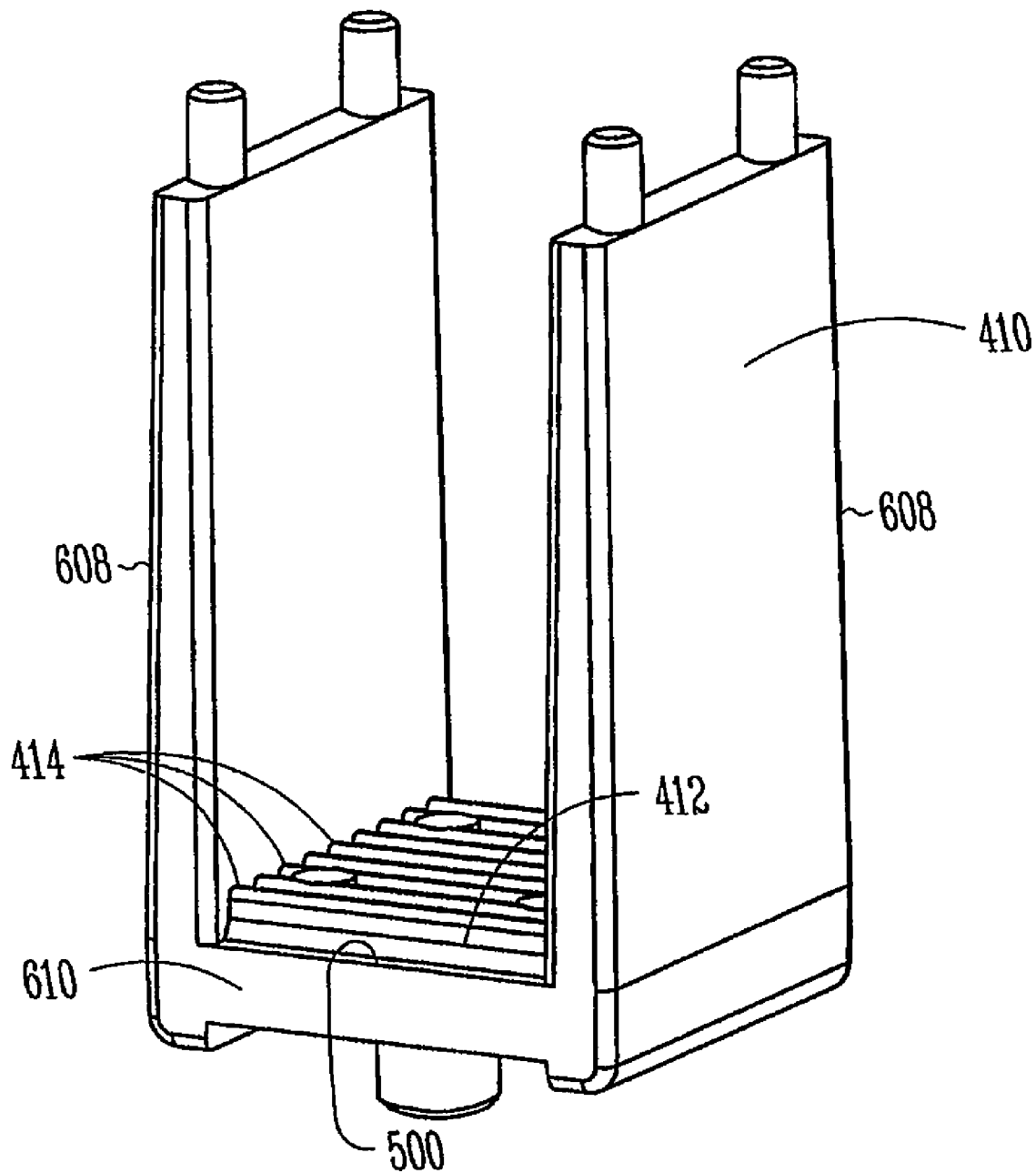
FIG. 5 is a perspective view of one example of the carriage.

The carriage assembly 406 includes a carriage 410 sized and shaped to move laterally (e.g., perpendicular to the flexible element 120 and the catheter body proximal end 102) to lock the carriage assembly 406 and the flexible element 120 coupled thereto in a desired position with respect to the support member 400 and allow retention of the deflectable distal tip 104 in a desired orientation. The carriage 410 is constructed with, but not limited to, plastics, metals and the like. In one example, the carriage 410 includes a blend of polycarbonate and acrylonitrile butadiene styrene (ABS). As shown in FIG. 4, the carriage 410 of the steering and locking system 401 includes a brake portion 412. The brake portion 412, in one option, includes at least one projection 414. Referring now to FIG. 5, in the example shown, multiple projections 414 are provided for enhanced locking between the support member 400 (FIG. 4) and the carriage 410 (further described below). Optionally, the brake portion 412 extends along an interior surface 500 of the carriage 410, and the projections 414 extend away from the interior surface 500 toward the support member 400.

Referring again to FIG. 4, the steering and locking system 401 includes a second brake portion 416 extending along at least a portion of the support member 400. The second brake portion 416 is sized and shaped to engage with the brake portion 412 (e.g., projections 414) and substantially prevent movement of the carriage assembly 406 along the handle assembly 150. In one option, the support member 400 includes a rack 418 sized and shaped to mate and interlock with the projections 414 of the carriage 410. The plurality of projections 414 along the carriage 410 provide multiple locking interfaces with the rack 418 to generate a strong locking force between the carriage 410 and the rack 418 of the support member 400 to securely retain the deflectable distal tip 104 in a deflected or straight orientation (FIGS. 1A, B, C). Optionally, the brake portions 412, 416 include other features adapted to lock the carriage assembly 406 in a desired position and thereby retain the deflectable distal tip in a desired orientation. In one example, the brake portions 412, 416 include a high friction surface such as a tacky substrate (e.g., rubber) or a contact adhesive. In another example, the brake portions 412, 416 include a high friction surface having a roughened substrate including, but not limited to, pitting, knurling and the like.

The brake portion 412 of the carriage 410 is shown engaged with the brake portion 416 of the support member 400 in FIG. 4. A biasing member 420, such as a spring, elastomeric material and the like is coupled with the carriage 410 and biases the carriage 410 toward the support member 400 and into engagement thereon. In one option, the biasing member 420 is a leaf spring coupled to the carriage 410 and extending between the carriage and the handle assembly 150. The biasing member 420 is constructed with, but not limited to, plastics, metals (e.g., stainless steel) and the like. The biasing member 420 is slidably coupled with the handle assembly 150 along a path 422, in another option. The biasing member 420 moves with the carriage assembly 406 along the path 422 and continually biases the carriage 410 including the brake portion 412 toward the support member 400 and into locking engagement with the brake portion 416. The biasing member 420 thereby ensures the carriage assembly 406 is locked in a desired position to locking the deflectable distal tip 104 (FIGS. 1A, B, C and 2) in a desired orientation.

Figure 6:
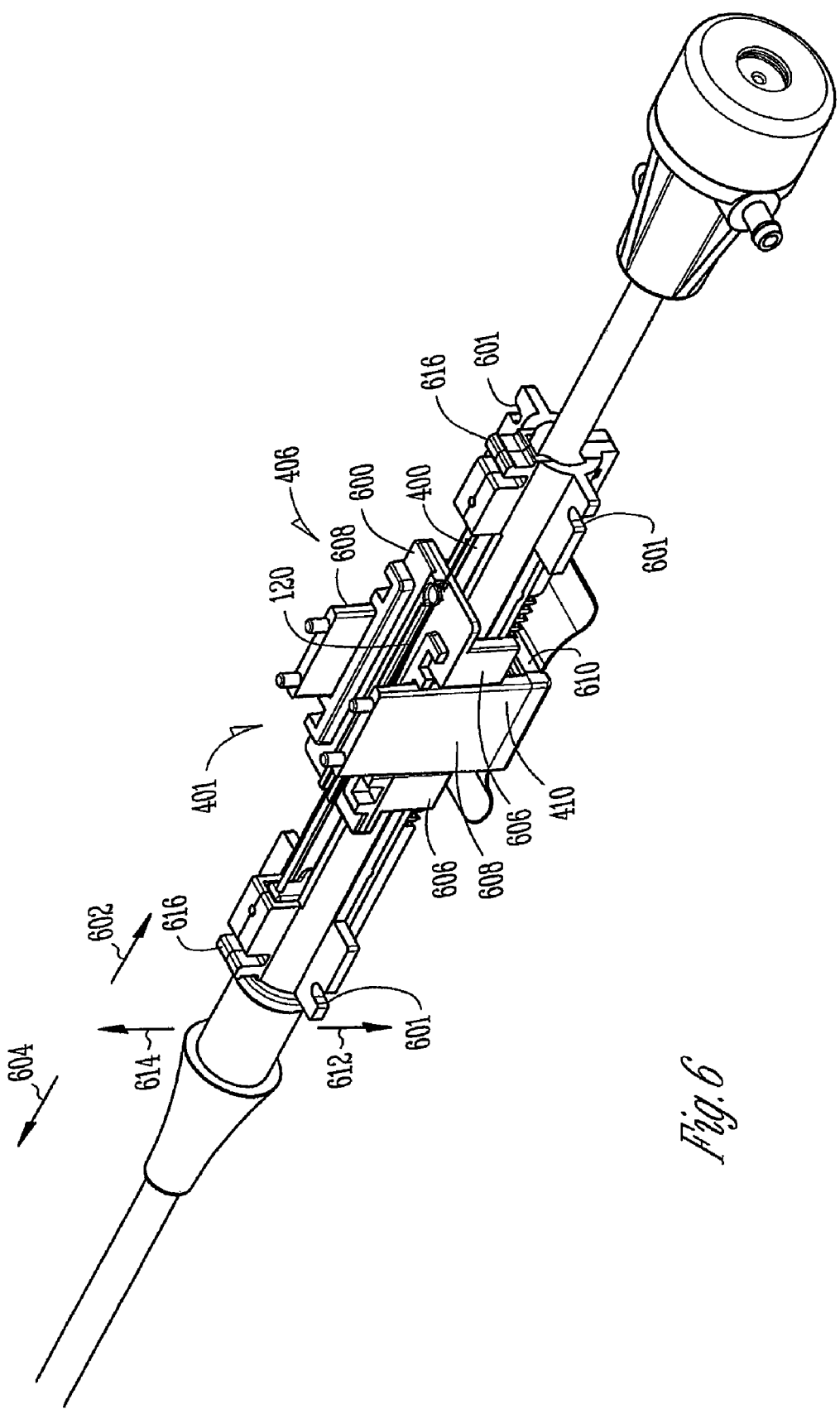
FIG. 6 is a perspective view of one example of the steering and locking system including the carriage assembly and the support member.

Referring now to FIG. 6, the carriage assembly 406 includes a retainer 600 moveably coupled with the carriage 410 and the support member 400. In one option, the retainer 600 is constructed with plastics, metals and the like. In one example, the retainer 600 is constructed with ULTEM a registered trademark of the General Electric Company. The retainer 600 is coupled with the flexible element 120 and transmits longitudinal movement of the carriage assembly 406 along the handle assembly 150 (FIG. 4) to the flexible element 120 thereby deflecting the distal tip 104 (FIGS. 1A, B, C). In another option, the retainer 600 is sized and shaped to slidably couple along the support member 400 coupled with the handle assembly 150. The retainer 600 moves in a proximal direction 602 and a distal direction 604 along the support member 400 thereby applying tension and compression, respectively to the flexible element 120 and deflecting the distal tip 104. The support member 400 is retained within the handle assembly 150, as described above with ribs 402 (FIG. 4). The ribs 402, optionally extend into recesses 601 of the support member 400 to substantially prevent movement of the support member 400 and catheter body relative to the handle assembly 150.

In another option, the retainer 600 is moved in the proximal and distal directions 602, 604 (i.e., longitudinally along the handle assembly 150) through movement of the carriage 410 coupled with the retainer 600. At least one of the carriage 410 and the retainer 600 includes a flange, such as flanges 606, sized and shaped to engage with the other of the carriage 410 and the retainer 600. As shown in FIG. 6, the flanges 606 extend from the retainer 410 and are engaged with the carriage 410 to transmit longitudinal movement of the carriage 410 to the retainer 600 and the flexible element 120 (FIG. 4) coupled thereto. The flanges 606 are slidably coupled with portions of the carriage 410 including struts 608, shown in FIGS. 5 and 6. The struts 608 extend around the support member 400 from a base 610 of the carriage 410 and ensure the brake portion 412 is adjacent to the brake portion 416 of the support member 400 during movement of the carriage assembly 406 (FIG. 4). Referring again to FIG. 6, the struts 608 and flanges 606 cooperate to permit lateral movement of the carriage 410 relative to, for instance, the retainer 600, support member 400 and the flexible element 120 while transmitting longitudinal movement to the retainer 600 to deflect the distal end 104 (FIGS. 1A, B, C). As shown in FIG. 6, the carriage 410 is slidably coupled to the retainer 600 and moveable in a first direction 612 and a second direction 614.

Referring again to FIGS. 4 and 6, the struts 608 of the carriage 410 are coupled with the actuator 304. The actuator 304 is movable longitudinally along the handle assembly 150 (as described above) and also moveably laterally with respect to the handle assembly when depressed (e.g., in the directions 612, 614 shown in FIG. 6). Because the actuator 304 is coupled with the carriage 410, lateral movement of the actuator 304 correspondingly moves the carriage 410 laterally. As shown in FIGS. 3 and 4, the handle assembly 150 includes, in one option, a depression 314 sized and shaped to receive the actuator 304 when the actuator is depressed from the position shown in FIG. 4 to contact the handle assembly 150 along the trough 424 of the depression 314.

As shown in FIG. 4, depression of the actuator 304 correspondingly depresses the carriage 410 coupled thereto and disengages the brake portion 412 of the carriage from the brake portion 416 of the support member 400 (e.g., the projections 414 of the carriage disengage from the rack 418 of the support member). In one option, depression of the actuator 304 overcomes the restoring force of the biasing member 420 and moves the carriage brake portion 412 away from the support member brake portion 416. Disengaging the brake portions 412, 416 unlocks the carriage assembly 406 and allows movement of the assembly 406 along the handle assembly 150. As shown in FIG. 6, the carriage assembly 406 (coupled with the actuator 304 shown in FIG. 4) is longitudinally moved in the directions 602, 604 to move the carriage 410 and correspondingly move the retainer 600 coupled to the carriage 410, as described above. The flexible element 120 coupled with the retainer 600 is placed in tension and/or compression when the carriage assembly 406 is longitudinally moved and the flexible element 120 deflects the deflectable distal tip 104 (FIGS. 1A, B, C). The distal tip 104 deflects according to the distance the actuator 304 and the carriage assembly 406 of the steering and locking system 401 are moved. The deflectable distal tip 104 thereby deflects into a range of disparate orientations according to the movement of the actuator 304. In another option, the actuator 304 is continually depressed to allow longitudinal movement of the carriage assembly 406. When the deflectable distal tip 104 is deflected into a desired orientation, the actuator 304 is released (i.e., no longer depressed) and the biasing member 420 biases the carriage 410 including the brake portion 412 into engagement with the brake portion 416 of the support member 400. Engagement of the brake portions 412, 416 (e.g., interlocking between the projections 414 and the rack 418) locks the carriage assembly 406 along the support member 400 and the handle assembly 150 thereby locking the deflectable distal tip 104 in the desired orientation. Optionally, the biasing member 420 provides sufficient restoring force to the carriage 410 to move the brake portions 412, 416 into engagement thereby allowing the brake portions to generate the locking force needed retain the distal tip 104 in the desired orientation.

Engagement of the brake portions 412, 416 (e.g., interlocking of the projections 414 with the rack 418) of the steering and locking system 401, as described above, ensures the deflectable distal tip 104 is locked in the desired orientation automatically with the release of the actuator 304. In any orientation achieved with the actuator 304 and carriage assembly 406, the deflectable distal tip 104 is held in that orientation by the engagement between the carriage assembly 406 and the support member 400 once the actuator 304 is released. Additional actuation of separate locking mechanisms is therefore not needed. The carriage assembly 406 and the support member 400, as described above, thereby combine deflection and locking of the distal tip 104 in a desired orientation into a single mechanism, such as the steering and locking system 401 using a single actuator (e.g., actuator 304).

Figure 7:
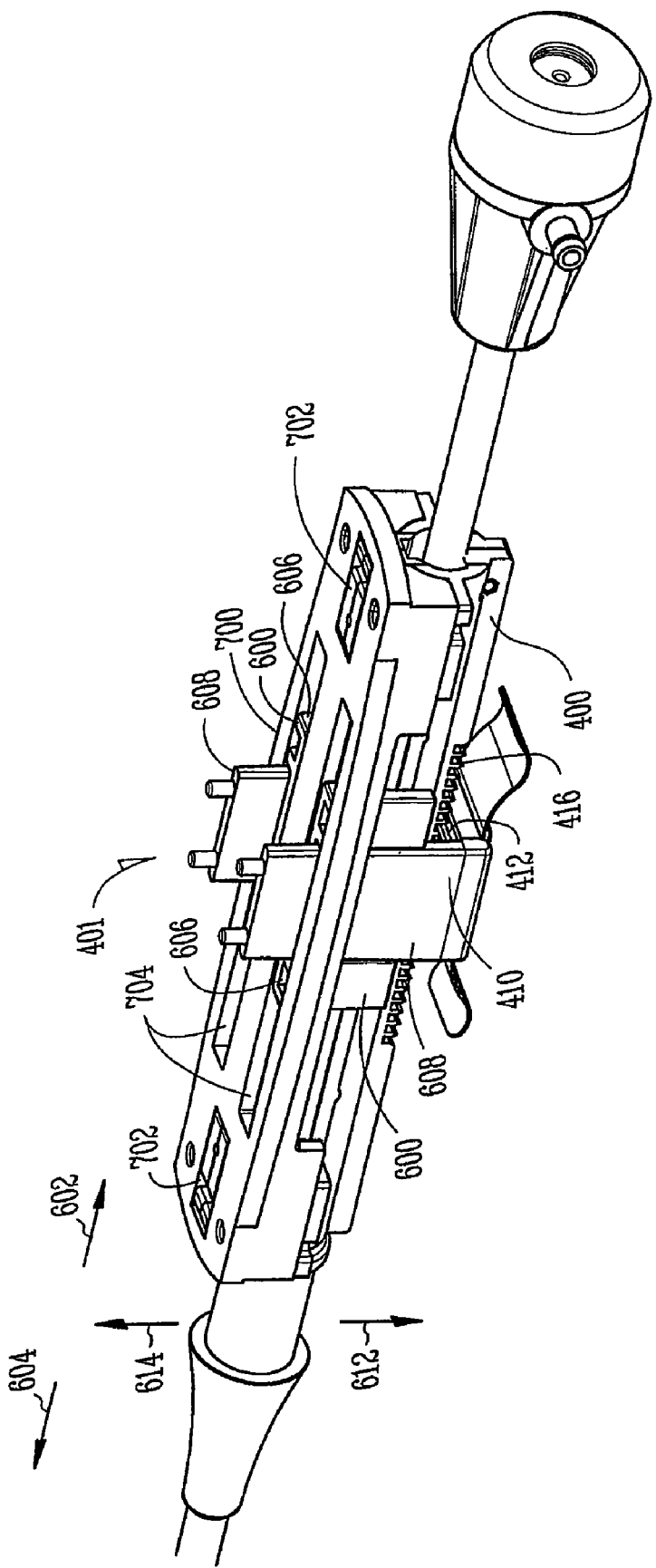
FIG. 7 is a perspective view of another example of the steering and locking system including the carriage guide member.

In another option, the steering and locking system 401 includes a guide, such as the carriage guide 700, shown in FIG. 7. The carriage guide 700, in one option, is coupled with the support member 400. As shown in FIG. 7, the carriage guide 700 includes alignment openings 702 sized and shaped to couple with the support member 400 and align the carriage guide 700 with the support member 400. In one option, shown in FIG. 6, the support member 400 includes fasteners, such as claws 616 sized and shaped to snap into engagement with corresponding features (e.g., recesses) in the alignment openings 702 when the carriage guide 700 is coupled with the support member 400. In another option, the carriage guide 700 is coupled with the support member 400 with adhesives, screws, bolts, pins, clamps and the like. The carriage guide 700 is constructed, optionally, with plastics, metals and the like. In one example, the carriage guide 700 includes nylon.

Referring again to FIG. 7, the carriage guide 700 includes at least one track 704 sized and shaped to slidably couple the strut 608 of the carriage 410 with the guide 700. As shown in FIG. 7, the carriage guide 700 includes two tracks 704. The tracks 704 and struts 608 are sized and shaped to permit longitudinal movement of the carriage 410 along the handle assembly 150 (FIG. 4). In one example, the carriage guide 700 permits movement of the carriage 410 in the directions 602, 604. Additionally, the carriage guide 700 is sized and shaped to allow lateral movement of the carriage 410 with respect to the handle assembly 150 and the support member 400. As described above, the carriage 410 moves laterally (e.g., in the directions 612, 614) to disengage the first brake portion 412 of the carriage 410 from the second brake portion 416 of the support member 400. The struts 608 slide laterally within the tracks 704 to move the brake portion 412 of the carriage 410 laterally relative to the support member 400.

In another option, the retainer 600 is captured between the support member 400 and the carriage guide 700. As shown in FIG. 7, the retainer 600 is slidably coupled between the carriage guide 700 and the support member 400 and moveable in the directions 602, 604 (i.e., longitudinally along the handle assembly 150 shown in FIG. 4). Optionally, the flanges 606 of the retainer 600 extend at least part way through the tracks 704 and are sized and shaped to slidably couple with the carriage guide 700. The tracks 704 cooperate with the flanges 606 to thereby guide the retainer 600 along the support member 400 and the carriage guide 700 when the retainer 600 is longitudinally moved. Additionally, the carriage guide 700 and the support member 400 are sized and shaped to substantially constrain the retainer 600 from moving laterally in the directions 612, 614 while permitting longitudinal movement. As shown in FIG. 7, the carriage guide 700 and the support member 400 are disposed over and under the retainer 600, respectively. In one option, the retainer 600 is substantially laterally static with respect to the flexible element 120 (FIG. 4), the support member 400, and the handle assembly 150 (FIG. 4).

As shown in FIG. 7, the carriage guide 700 and the support member 400 cooperate to allow movement of the carriage assembly 406 (e.g., the carriage 410 and the retainer 600) longitudinally along the support member 400 and handle assembly 150 and thereby permit deflection of the distal tip 104 (FIGS. 1A, B, C and 2) through tension and compression of the flexible element 120 (FIG. 4). Moreover, the carriage guide 700 and the support member 400 cooperate to permit lateral movement of the carriage 410 and substantially prevent lateral movement of the retainer 600, as described above. Optionally, the carriage guide 700 has guide features including rails, grooves, channels and the like sized and shaped to permit movement of the carriage assembly 406 in the longitudinal direction and substantially prevent lateral movement of the retainer 600.

Figure 8:
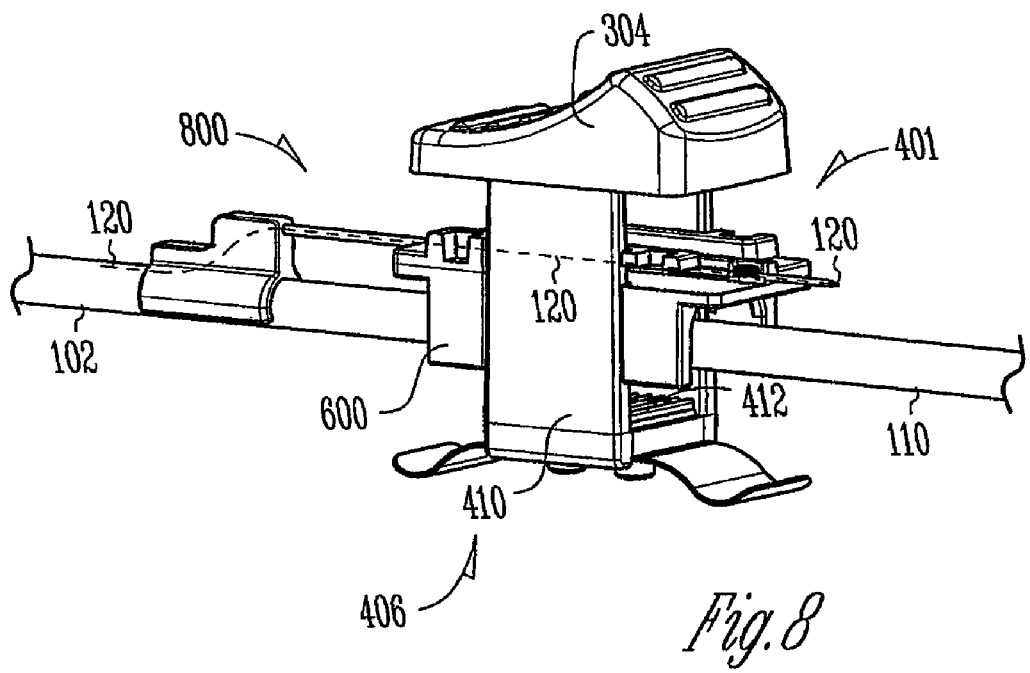
FIG. 8 is a perspective view of another example of the carriage assembly and a portion of the tube assembly.

FIG. 8 is a perspective view of a portion of the steering and locking system 401 including the carriage assembly 406 coupled around the proximal end 102 of the catheter body 110. The carriage assembly 406 is shown coupled with a tube assembly 800. In one option, the tube assembly 800 is coupled with the retainer 600. The tube assembly 800 is coupled around the flexible element 120 and has an inner diameter slightly larger than the outer diameter of the flexible element 120, in another option. The tube assembly 800 thereby provides support to the flexible element 120 and constrains the flexible element 120 from moving laterally and substantially prevents buckling of the flexible element 120. The support against buckling provided by the tube assembly 800 allows loading of the flexible element 120 in compression to permit pushing of the flexible element 120 and deflection of the distal tip 104 (FIGS. 1A, B, C and 2) in an opposing direction to deflection caused by tension. Optionally, the tube assembly 800 extends between the retainer 600 and the sidewall exit 403 (FIG. 4) of the flexible element 120 to provide support therebetween. The flexible element 120 is thereby constrained from moving laterally by the tube assembly 800 between the retainer 600 and sidewall exit 403, and the sidewall 124 (FIG. 2) between the sidewall exit 403 and the distal tip 104.

Figure 9:
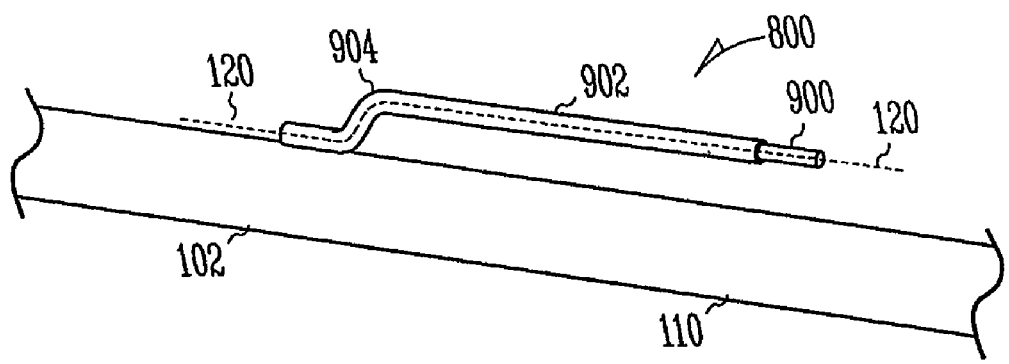
FIG. 9 is a perspective view of one example of the tube assembly.

FIG. 9, is a perspective view of the proximal end 102 of the catheter body 110 and one example of the tube assembly 800 without the carriage assembly 406 (FIG. 8) coupled thereto for clarity. As shown in FIG. 9, in one option, the tube assembly 800 includes a first tube 900 slidably coupled with a second tube 902 both of which are coupled around the flexible element 120. The first tube 900 has an inner diameter slightly larger than the outer diameter of the flexible element 120 and constrains the flexible element 120 from moving laterally (e.g., buckling), as described above. The first tube 900 is coupled with the retainer 600 (FIGS. 6 and 8), optionally, and moves with the retainer 600 and the flexible element 120 when the carriage assembly 406 is moved longitudinally along the handle assembly 150 (FIG. 4), as described above.

The second tube 902 has an inner diameter slightly larger than the outer diameter of the first tube 900 to permit sliding movement between the tubes 900, 902 throughout a range of travel of the carriage assembly 406 in the handle assembly 150. The second tube 902 substantially prevents lateral movement of the first tube 900 because of the tight tolerances between inner diameter and outer diameter of the respective tubes 900, 902. The first tube 900 extends through a portion of the second tube 902. The second tube 902 has a sufficiently small inner diameter to substantially prevent buckling of the flexible element 120 where the element 120 exits the first tube 900 and is received within the second tube 902. As shown in FIG. 9, the second tube has a curved portion 904, in another option. The small inner diameter of the second tube 902 constrains the flexible element 120 and permits movement of the element 120 through the curved portion 904 according to the path defined by the inner diameter of the second tube 902 in the portion 904.

The first and second tubes 900, 902, as described above, thereby substantially prevent lateral movement and buckling of the flexible element 120. The first and second tube 900, 902 allow loading of the flexible element 120 in compression to permit deflection of the distal tip 104 (FIGS. 1A, B, C and 2) through pushing of the flexible element 120. In yet another option, the second tube 902 is coupled along the catheter body 110, for instance with a flexible element guide (described below), and is therefore static relative to movement of the carriage assembly 406 (FIG. 8). The first tube 900 is coupled with the retainer 600 of the carriage assembly 406, as described below. Longitudinal movement of the carriage assembly 406 correspondingly moves the flexible element 120 and the first tube 900 coupled therearound with respect to the second tube 902. Because of the slidable coupling between the first and second tubes 902, the flexible element 120 is supported throughout the range of travel of the carriage assembly 406 along the handle assembly 150. Optionally, the tube assembly 800 includes a portion of the handle assembly 150 sized and shaped to slidably couple with the first tube 900. For instance, the handle assembly 150 is molded, machined and the like to slidably couple with the first tube 900 in a similar manner as the second tube 902. The handle assembly 150 thereby cooperates with the first tube 900 to substantially prevent lateral movement of the flexible element 120 including buckling. One example of a tube assembly sized and shaped to constrain lateral movement is shown in Pudelko et al., U.S. patent application Ser. No. 10/670,150, filed on Sep. 24, 2003, entitled "BI-DIRECTIONAL CATHETER ASSEMBLY AND METHOD THEREFOR," which is assigned to the assignee of the present application and incorporated by reference herein in its entirety.

Figure 10:
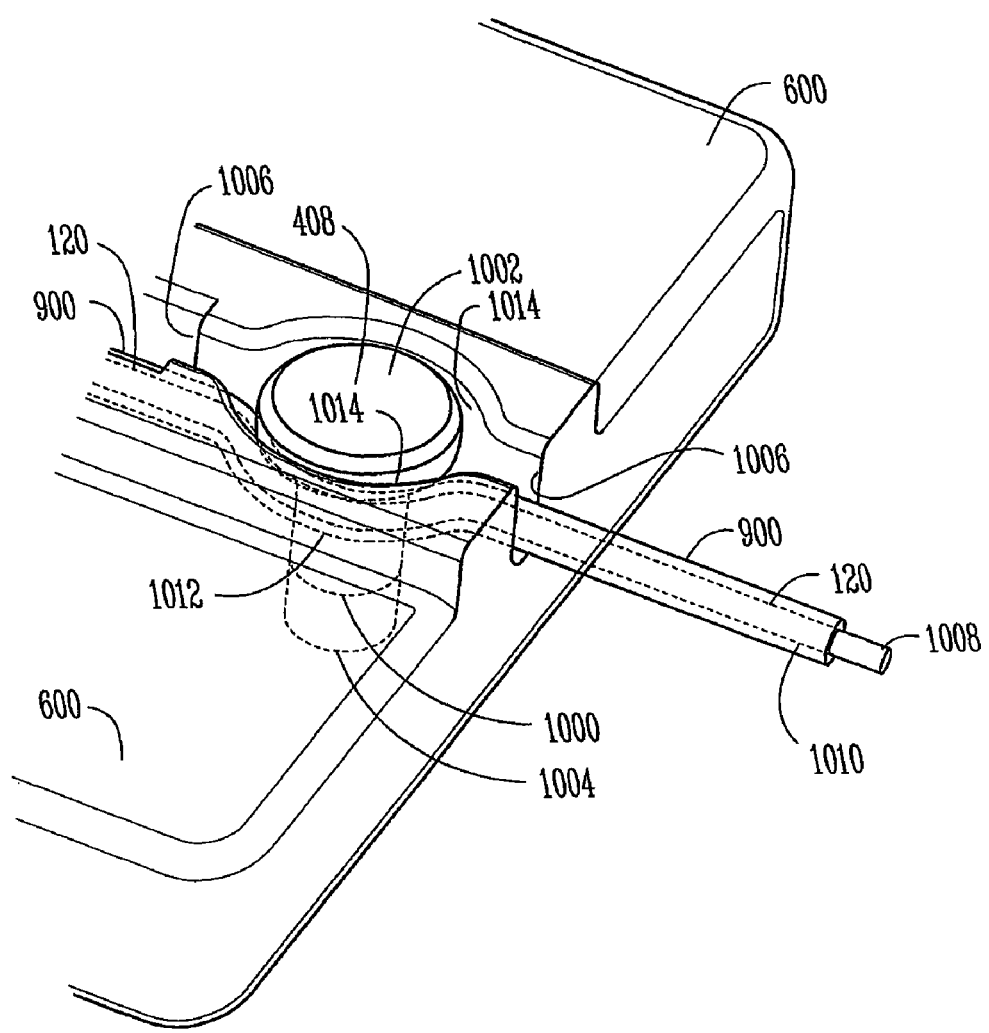
FIG. 10 is a detailed perspective view of a portion of a retainer and the tube assembly.

FIG. 10 shows the retainer 600, the first tube 900 of the tube assembly 800 coupled with the retainer 600 and the retaining pin 408. As shown in FIG. 10, the retaining pin 408 includes a neck 1000 and a head 1002. The neck 1000, in one option, has an outer perimeter slightly larger than the inner perimeter of a pin opening 1004 of the retainer 600. The neck 1000 creates an interference fit with the retainer 600 when the retaining pin 408 is placed in the pin opening 1004 thereby securely fastening the retaining pin 408 to the retainer 600. The tube 900, in another option, extends through a slot 1006 of the retainer 600 and around the neck 1000 of the retaining pin 408. The head 1002 extends over at least a portion of the tube 900 to substantially prevent lateral movement of the tube 900 out of the slot 1006. As described above, the flexible element 120 extends through the tube 900. As shown in FIG. 10, the flexible element 120 extends with the tube 900 through the retainer 600. The flexible element 120 and the tube 900 extend proximally from the retainer 600 and provide corresponding free ends 1008, 1010. The tube 900 is coupled with the flexible element 120, for instance, by crimping the free end 1010 of the tube 900 around the free end 1008 of the flexible element 120. The tube 900 grasps the flexible element 120 and thereby immobilizes the flexible element 120 within the tube 900. In yet another option, the tube 900 is coupled with the flexible element 120 with a weld, adhesives, mechanical fasteners and the like.

In one option, the tube 900 includes a non-linear portion, such as a curved portion 1012 sized and shaped to wrap around at least a portion of the neck 1000 of the retaining pin 408. In another option, the non-linear portion includes, but is not limited to, spiraled, zig-zag, serpentine geometries and the like. The slot 1006 of the retainer 600 includes a non-linear portion, such as a curved slot portion 1014, having a similar geometry to the curved portion 1012 of the tube 900. The curved portion 1012 of the tube 900 is coupled between the retaining pin 408 and the retainer 600 within the curved slot portion 1014. The engagement of the curved portion 1012 with retaining pin 408 and the retainer 600 in the curved slot portion 1014 substantially prevents longitudinal movement of the tube 900 with respect to the retainer 600. The tube 900 is locked in place within the retainer 600 by the curved portion 1012. In another option, where the tube 900 is coupled with the flexible element 120 (e.g., by crimping as described above), the flexible element 120 is substantially prevented from moving longitudinally with respect to the retainer 600. Longitudinal movement of the carriage assembly 400 (FIG. 4), including the retainer 600, thereby moves the tube 900 and the flexible element 120 to deflect the distal tip 104, as described above.

Referring again to FIGS. 7-9, a portion of the carriage assembly 406 of the steering and locking system 401, such as the retainer 600, is constrained from moving laterally (e.g., in the directions 612, 614), as described above. The carriage guide 700 and the support member 400 cooperate, in one option, to constrain lateral movement of the retainer 600 while allowing longitudinal movement of the carriage assembly 406 along the handle assembly 150 (FIG. 4). The laterally static retainer 600 cooperates with the tube assembly 800, shown in FIGS. 8 and 9, to substantially prevent lateral movement of the flexible element 120 during longitudinal movement of the carriage assembly 120 to cause deflection in the distal tip 104 of the catheter body 110 (FIGS. 1A, B, C). Because the flexible element 120 is substantially prevented from moving laterally (e.g., buckling) with respect to the handle assembly 150, the flexible element 120 is loadable in compression to deflect the distal tip 104 in an opposed direction to the deflection caused with tensioning of the flexible element. In another option, the carriage assembly 406 is moveable in the proximal and distal directions 602, 604 to pull and push the flexible element 120 and thereby deflect the distal tip 10 in opposed directions. The cooperation of the retainer 600 and the tube assembly 800 permits active deflection of the distal tip 104 with compression of the flexible element 120 from deflected positions, such as the positions shown in FIGS. 1A, C. The passive deflection provided by the natural elasticity of the catheter body 110 and/or engagement of the catheter body 110 with surfaces such as vasculature is thereby unnecessary for control of the deflectable distal tip 104. Instead, the steering and locking system 401 actively controls deflection of the distal tip 104 in any direction according to movement of the carriage assembly 406.

As shown in FIGS. 7-9, in another option, the retainer 600 and the tube assembly 800 cooperate to substantially prevent lateral movement of the flexible element 120 and allow for tension and compression of the flexible element 120 while the carriage 410 is permitted to move laterally to engage and disengage the brake portions 412, 416 and correspondingly lock and unlock to retain the deflectable distal tip 104 in a desired orientation. The steering and locking system 401 (e.g., the carriage assembly 406 and the support member 400) thereby deflects the distal tip 104 with tension and compression of the flexible element 120, and locks the distal tip 104 in an orientation through engagement of the brake portions 412, 416. Deflection of the distal tip 104 and locking of the tip 104 in a desired orientation are consolidated into a single assembly, the steering and locking system 401. Additionally, the steering and locking system 401 is operated with a single control, the actuator 304 (FIGS. 3 and 8) to deflect the distal tip 104 and lock the tip in the desired orientation.

Figure 11A:
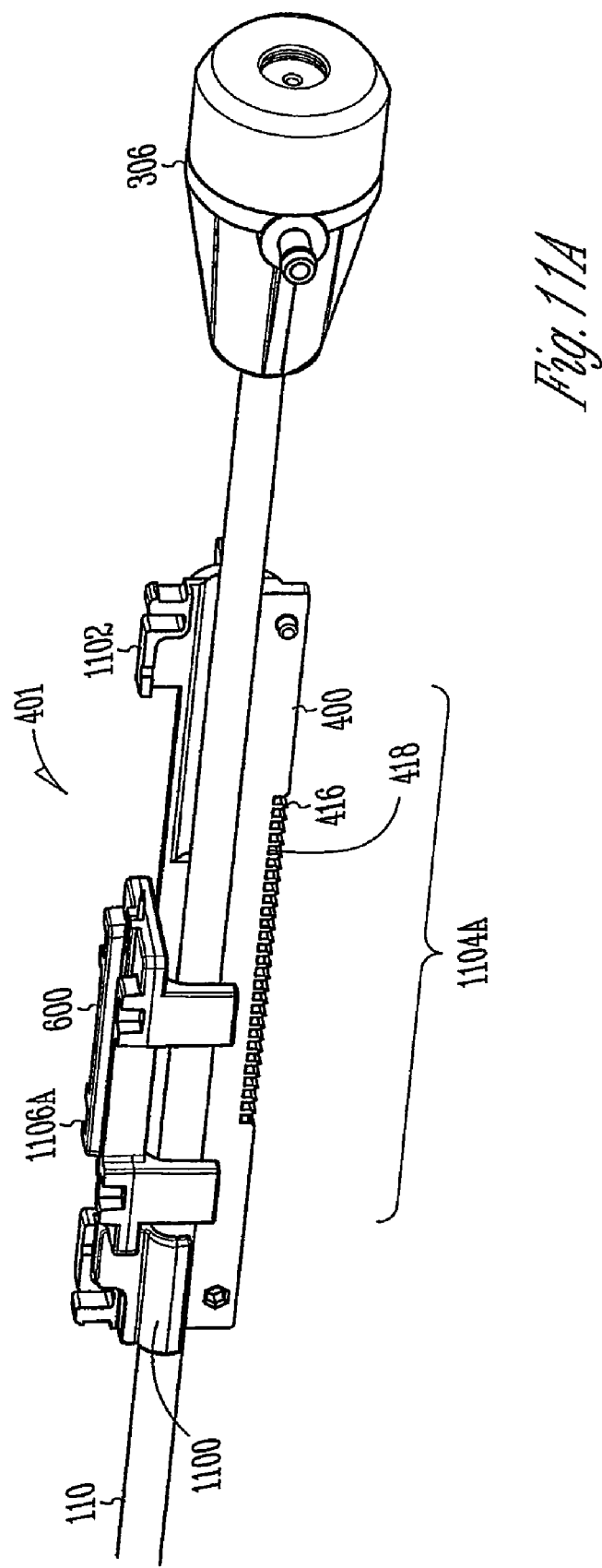
FIG. 11A is a perspective view of yet another example of the steering and locking system including the carriage assembly having a first range of travel between the flexible element guide and the proximal stop.

FIG. 11A, B show another example of the steering and locking system 401 including the retainer 600 and the support member 400 (only a portion of the support member 400 is shown in FIGS. 11A, B for clarity) coupled along the catheter body 110. In one option, the catheter body 110 includes a flexible element guide 1100 sized and shaped to couple around the catheter body 110 at the sidewall exit 403 (FIG. 4). The flexible element guide 1100 extends away from the catheter body 110. Optionally, the flexible element guide 1100 couples with the second tube 902 (FIG. 9) and retains the second tube 902 along the catheter body 110. The flexible element guide 1100 is constructed with, but not limited to, plastics, metals and the like. In one example, the retainer 600 is constructed with PEBAX.

In another option, the support member 400 includes a proximal stop 1102 extending from the support member 400. The proximal stop 1102, in yet another option, is proximal to the brake portion 416 (e.g., the rack 418). The retainer 600 moves along the handle assembly 150 (FIG. 4) and the support member 400, as described above. The flexible element guide 1100 and the proximal stop 1102 are sized and shaped to engage with the retainer 600 and substantially prevent movement of the retainer 600 proximal to the proximal stop 1102 and distal to the flexible element guide 1100. The flexible element guide 1100 and the proximal stop 1102 thereby define a range of travel for the retainer 600. As described above, the retainer 600 is coupled with the carriage 410 (FIG. 4) and moves longitudinally with the carriage 410. The range of travel defined by the flexible element guide 1100 and the proximal stop 1102 is thereby also the range of travel for the carriage 410. Actuation of the carriage assembly 406 (e.g., the carriage 410 and the retainer 600) through the actuator 304 (FIGS. 3 and 4) is limited to the range of travel defined by the flexible element guide 100 and the proximal stop 1102.

A first range of travel 1104A is shown in FIG. 11A between the flexible element guide 1100 and the proximal stop 1102. The retainer 600 is free to move longitudinally between the guide 1100 and the stop 1102 (i.e., through the range of travel 1104A) and thereby deflect the distal tip 104 (FIGS. 1A, B, C) through corresponding compression and tension of the flexible element 120 (FIGS. 2 and 4). A second range of travel 1104B is shown in FIG. 11B. Like the first range of travel 1104A, the retainer 600 is moveable between the flexible element guide 1100 and the proximal stop 1102. However, the second range of travel 1104B is shorter than the first range of travel 1104A because the support member 400 including the proximal stop 1102 is coupled closer to the flexible element guide 1100. Conversely, the support member 400 and the proximal stop 1102 are coupled more proximally relative to the flexible element guide 1100 to provide the longer first range of travel 1104A. A variety of ranges of travel are thereby available by changing the location the support member 400 couples around the catheter body 110. In one option, once the support member 400 is coupled around the catheter body 110 both are positioned within a handle assembly 150 adapted to couple with the support member 400 as described above. Optionally, the handle assembly 150 is a standard handle design usable with a variety of configurations of the support member 400 and the catheter body 110 to define a corresponding variety of ranges of travel (e.g., ranges of travel 1104A, B). Coupling the support member 400 with the handle assembly 150 allows for the variety of ranges of travel while still using a single handle design.

In one option, the longer range of travel 1104A (FIG. 11A) is used with the catheter body 110 having a deflectable distal tip 104 (FIGS. 1A, B, C) with a large range of deflection. The longer range of travel 1104A permits full use of the distal tip 104 deflection range. In another option, the longer range of travel 1104A is used with a catheter body 110 that is relatively rigid (e.g., formed with a stiff material or having a larger diameter). The longer range of travel 1104A permits the carriage assembly 406 (FIG. 4) to pull and push the flexible element 120 a sufficient amount to deflect the rigid distal tip 104 into a desired orientation. Optionally, the shorter range of deflection 1104B (FIG. 11B) is used with a catheter body 110 constructed with a relatively flexible material so that only a small range of motion is needed for the carriage assembly 406 to deflect the distal tip 104 through a desired range of deflected orientations. In yet another option, the deflectable distal tip 104 needs only a limited range of deflection and the shorter range of travel 1104B provided by the proximal stop 1102 and the flexible element guide 1100 ensures the carriage assembly 406 will only deflect the distal tip 104 within that desired deflection range. The ranges of travel 1104A, B are only two examples of the range of travel available by coupling the support member 400 at different locations along the catheter body 110. A variety of ranges of travel are available where the proximal stop 1102 of the support member 400 is coupled proximally further and distally closer to the flexible element guide 1100.

Referring again to FIGS. 11A, B, in another option, the support member 400 is coupled along the catheter body 110 at a predetermined location to establish neutral home positions 1106A, B along the support member 400 within the ranges of travel 1104A, B, respectively for the carriage assembly 406 (FIG. 4) including the retainer 600. In yet another option, the length of the flexible element 120 (FIG. 4) cooperates with the position of the support member 400 to determine the home positions 1106A, B. The home positions 1106A, B provide a corresponding neutral (straight) orientation of the distal tip 104 shown in FIG. 1B, optionally.

As shown in FIG. 11A, the home position 1106A is near the flexible element guide 1100 and remote from the proximal stop 1102. The carriage assembly 406, including the retainer 600, is thereby able to move a relatively small distance distally and a relatively large distance proximally. The deflectable distal tip 104 of the catheter assembly 100 with this range of travel 1104A and home position 1106A is able to deflect in a first direction, for instance as shown in FIG. 1C, and able to deflect a larger amount in a second direction, for instance up to at least the orientation shown in FIG. 1A. As shown in FIG. 11B, the support member 400 is coupled with the catheter body 110 so the home position 1106B is positioned more equidistantly between the flexible element guide 1100 and the proximal stop 1102 than with the home position 1106A shown in FIG. 6. In still another option, the length of the flexible element 120 cooperates with the position of the support member 400 on the catheter body 110 to provide the home position 1106B. The deflectable distal tip 104 of the catheter assembly 100 with this range of travel 1104B and home position 1106B is able to move at least between the orientation shown in FIG. 1C and an orientation between those shown in FIGS. 1A and 1B.

Referring again to FIG. 4, in operation, the actuator 304 is depressed into or toward the depression 314. Movement of the actuator 304 laterally correspondingly moves the carriage 410 of the steering and locking system 401 laterally with respect to the flexible element 120 and the handle assembly 150. Depressing the actuator 304 overcomes the restoring force of the biasing device 420 adapted to engage the first brake portion 412 of the carriage 410 with the second brake portion 416 of the support member 400. The first brake portion 412 including, in one option, the projections 414 is thereby disengaged from the second brake portion 416 to permit longitudinal movement of the carriage assembly 406 (including the carriage 410 and the retainer 600 shown in FIG. 6) along the handle assembly 150 and the support member 400. Movement of the carriage assembly 406 correspondingly moves the flexible element 120 coupled thereon. The flexible element 120 is loaded in compression and/or tension as desired with respective distal and proximal movement of the carriage assembly 406. In another option, compression of the flexible element 120 deflects the distal tip 104 into the orientation shown in FIG. 1C. In yet another option, tension of the flexible element 120 deflects the distal tip 104 into the orientation shown in FIG. 1A. When a desired orientation of the deflectable distal tip 104 is obtained, including a straight orientation as shown in FIG. 1B, the actuator 304 is released allowing the biasing member 420 to push the carriage 410 and the first brake portion 412 into engagement with the second brake portion 416 of the support member 400. Optionally, engagement of the projections 414 with the rack 418 creates an interlocking fit therebetween that substantially prevents movement of the carriage assembly 406 along the handle assembly 150. In still another option, a biasing member 420 providing a relatively weak restoring force is used to bias the carriage assembly 406 because the projections 414 and the rack 418 lock the carriage assembly 406 in place once engaged. The steering and locking system 401 including the carriage assembly 406 and the support member 400 thereby provides steering and locking functions with a single assembly using a single actuator 304.

Referring now to FIGS. 6-9, the retainer 600 of the carriage assembly 406 is sized and shaped to permit lateral movement of the carriage 410 relative to the flexible element 120 (FIG. 4) while the retainer 600 remains laterally static. In one option, the retainer 600 includes flanges 606 that transmit longitudinal movement of the carriage 410 to the retainer 600 and allow sliding lateral movement of the carriage 410 with respect to the retainer 600. As shown in FIG. 7, optionally, the carriage guide 700 is coupled over the retainer 600 and the retainer 600 is slidably coupled between the carriage guide 700 and the support member 400. The carriage guide 700 and the support member 400 cooperate to substantially prevent lateral movement of the retainer 600 (e.g., movement in the directions 612, 614). The retainer 600 thereby retains the flexible element 120 in substantially laterally static position while the carriage assembly 406 moves longitudinally (e.g., in directions 602, 604) along the handle assembly 150 (FIG. 4) and the support member 400. The moveable coupling between the carriage 410 and the retainer 600 allows the first and second brake portions 412, 416 to engage with lateral movement of the carriage 410 and thereby lock the carriage assembly 406 along the support member 400 in the handle assembly 150 without laterally moving the retainer 600.

In another option, the retainer 600 cooperates with the tube assembly 800 shown in FIGS. 8 and 9 to substantially prevent lateral movement of the flexible element 120 when the element 120 is loaded in tension and compression (e.g., moved in the directions 602, 604 shown in FIG. 6). The first and second tubes 900, 902, optionally, have inner diameters slightly larger than the outer diameter of the flexible element 120 to constrain movement of the flexible element and substantially prevent buckling when the element 120 is loaded in compression. The carriage assembly 406 (FIG. 6) is thereby moveable in the directions 602, 604 to pull and push the flexible element 120 and correspondingly deflect the distal tip 104 into at least the orientations shown in FIGS. 1A, B, C. Additionally, the retainer 600 and the tube assembly 800 cooperate to allow active deflection of the distal tip 104 through compression and tension of the flexible element without requiring passive deflection provide by the natural elasticity of the catheter body 110 (FIGS. 1A, B, C) and/or engagement with vasculature surrounding the catheter body 110.

FIG. 12 is a block diagram showing one example of a method 1200 for making a deflectable catheter assembly. At 1202, a flexible element is coupled to a deflectable distal tip of a catheter shaft. At 1204 a support member is coupled around a proximal portion of the catheter shaft. The support member includes a first brake portion, such as a rack, high friction surface and the like, extending along at least a portion of the support member. At 1206, a handle is coupled to the support member. In one option, the handle is coupled around a hemostasis valve, and the hemostasis valve is in communication with a delivery lumen of the catheter shaft. At 1208, a carriage assembly is moveably coupled with the handle. The carriage assembly includes a carriage having a second brake portion (e.g., projection, high friction surface and the like) sized and shaped to engage with at least a portion of the first brake portion. At 1210, a flexible element is coupled with the carriage assembly. At 1212, a biasing device is coupled between the carriage assembly and the handle. The biasing device is moveably coupled along the handle, and is adapted to bias the second brake portion into engagement with the first brake portion. Optionally, the method 1200 includes coupling an actuator with the carriage. The actuator is adapted to move the carriage between a first position where the second brake portion is engaged with the first brake portion and a second position where the second brake portion is disengaged with the first brake portion.

In one option, the method 1200 includes coupling a flexible element guide with the catheter shaft. The flexible element extends outside of the catheter shaft at the flexible element guide. Coupling the support member around the proximal portion of the catheter shaft includes, in another option, coupling the support member around the proximal portion of the catheter shaft, and the support member includes a proximal stop proximal to the first brake portion. The carriage assembly has a range of travel along the handle between the flexible element guide and the proximal stop. Optionally, the method 1200 includes coupling the support member around a predetermined location of the catheter shaft to define the range of travel.

In another option, moveably coupling the carriage assembly with the handle includes slidably coupling a retainer with the carriage, and the flexible element is coupled with the retainer. The retainer is sized and shaped to move with the carriage longitudinally along the handle, and the retainer is sized and shaped to remain substantially laterally static relative to the flexible element. Optionally, the method 1200 includes slidably coupling a carriage guide with the carriage assembly, and the carriage guide is sized and shaped to permit lateral movement of the carriage relative to the flexible element and substantially prevent lateral movement of the retainer. The carriage guide is sized and shaped to permit movement of the carriage assembly longitudinally along the handle.

Optionally, the method 1200 includes moving the carriage laterally relative to the flexible element, and disengaging the second brake portion from the first brake portion. The carriage assembly is moved longitudinally along the handle and the flexible element moves with the carriage assembly and pulls or pushes the deflectable distal tip. The flexible element deflects the deflectable distal tip between a first orientation and a second orientation. The method 1200 further includes retaining the deflectable distal tip in the second orientation when the biasing device moves the second brake portion into engagement with the first brake portion.

The above described deflectable catheter provides a steering and locking system capable of locking the deflectable distal tip in a desired deflected position. The carriage and retainer cooperate with the support member to longitudinally move the flexible element to deflect the distal tip and lock the distal tip in a desired deflected position. The steering and locking system substantially prevents movement of the carriage proximally or distally, thereby substantially preventing further undesired deflection of the catheter or straightening when the carriage is in the locked position. Optionally, the steering and locking system automatically locks the catheter in a desired orientation by releasing the actuator. In one option, the carriage includes the second brake portion having, for instance, multiple projections that provide a strong locking force between the carriage and the first brake portion (e.g., rack, high friction surface and the like) of the support member to securely retain the distal tip of the catheter in a deflected orientation.

As described above, the carriage assembly including the carriage and retainer are operated to deflect the distal tip and lock the distal tip in a desired deflected position. The carriage assembly thereby consolidates the deflection system with the locking system into the single steering and locking system to simplify use of the catheter. In another option, a single actuator is used to control both the deflection and locking of the deflectable catheter. Additional controls and the like are unnecessary. Further, combining the deflection and locking features decreases labor and manufacturing costs. Moreover, in another option, the catheter handle includes a hemostasis valve and/or flush port therein to further simplify use of the deflectable catheter.

Additionally, the support member provides a brake portion for locking the carriage in place and is a structural support to the catheter shaft during deflection and traversing of the vasculature. Moreover, the support member is coupled along the catheter shaft at a predetermined location to provide a range of travel for the carriage, and thereby a range of deflection of the distal tip. The space between the proximal stop of the support member and the flexible element guide along the catheter shaft defines the range of travel and corresponding range of deflection for the distal tip. Coupling the support member distally toward the flexible element guide provides a short range of travel (e.g., for thin walled catheters). Coupling the support member proximally away from the flexible element guide provides a longer range of travel (e.g., for thicker catheters, greater deflection ranges, and the like). Further, coupling the support member at the predetermined location also establishes a neutral position for the carriage where the deflectable distal tip assumes an undeflected orientation. The support member is coupled along the catheter body at a variety of locations to define a corresponding variety of ranges of travel. In yet another option, the support member is coupled with a standard handle sized and shaped to receive the support member. A single handle is thereby used with the same support member no matter what the range of travel is of the carriage assembly thereby decreasing labor and manufacturing costs.

Further, the retainer and tube assembly substantially prevent buckling of the flexible element thereby allowing tension and compression loading of the flexible element. Because the flexible element is constrained from moving laterally between the retainer and the deflectable distal tip the element is loadable in tension and compression to provide bi-directional deflection of the distal tip. In another option, loading the flexible element in compression permits active straightening of the deflected catheter thereby providing active control for deflection and straightening with the carriage assembly (i.e., the natural catheter elasticity does not unpredictably control straightening of the distal tip). The carriage guide, in yet another option, facilitates longitudinal movement of the carriage and the retainer while holding the retainer in a substantially laterally static position with respect to the flexible element. The carriage guide thereby ensures the retainer cooperates with the tube assembly to keep the flexible element static, while permitting longitudinal movement of the carriage assembly for deflection of the distal tip. Additionally, the carriage guide permits lateral movement of the carriage to engage and disengage the second brake portion of the carriage with the first brake portion of the support member.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

What is claimed is:

1. A method for using a catheter comprising:
    deflecting a catheter deflectable distal tip and locking the catheter deflectable distal tip in a desired orientation with only movement of an actuator, the actuator engaged with a carriage, including:
        depressing the actuator and the carriage relative to a handle;
        moving the actuator, the carriage and a retainer proximally and distally relative to the catheter deflectable distal tip, the actuator is attached to a flexible element anchored in the catheter deflectable distal tip by the retainer movably coupled with the carriage, wherein:
            proximal movement of the actuator loads the flexible element in tension and pulls the deflectable distal tip in a first direction, and
            distal movement of the actuator loads the flexible element in compression and transmits a pushing force to the deflectable distal tip, and the transmitted pushing force deflects the deflectable distal tip in a second opposed direction; and
        releasing the actuator relative to the handle, and the actuator locks the flexible element in the position at release and correspondingly locks the deflectable distal tip in the desired orientation, wherein the retainer and the flexible element are laterally static relative to the handle during depressing and releasing.

2. The method of claim 1, wherein depressing the actuator relative to the handle disengages the actuator from a first brake portion in the handle and permits the proximal and distal actuator movement, where the actuator includes a second brake portion sized and shaped to engage with the first brake portion and lock the flexible element in position.

3. The method of claim 2, wherein releasing the actuator relative to the handle engages the second brake portion with the first brake portion and locks the flexible element in the position at release.

4. The method of claim 3, wherein releasing the actuator relative to the handle includes biasing the second brake portion of the actuator into engagement with the first brake portion.

5. The method of claim 1, wherein depressing and releasing of the actuator moves the actuator laterally relative to the direction of proximal and distal actuator movement.

6. The method of claim 1, wherein the actuator includes a retainer attached to the flexible element and a carriage movably coupled with the retainer, and:
    depressing and releasing of the actuator moves the carriage laterally relative to the retainer, the flexible element and the direction of proximal and distal movement of the actuator, and
    proximal and distal movement of the actuator moves the carriage together with the retainer.

7. The method of claim 6 further comprising slidably engaging the retainer along a catheter body throughout proximal and distal actuator movement and depressing and releasing of the actuator, wherein the retainer is laterally static relative to the catheter body.

8. The method of claim 1, wherein distal movement of the actuator includes constraining lateral movement of the flexible element with a flexible element guide extending outside of a catheter body, and the flexible element guide is slidably engaged around the flexible element extending from the actuator to the catheter body.

9. A method for using a catheter comprising:
deflecting a catheter deflectable distal tip and locking the catheter deflectable distal tip in a desired orientation with movement of an actuator relative to a handle and a catheter body from a first location to a second location, wherein the actuator is released and in a locked configuration at the first location, the actuator is engaged with a carriage, and deflecting the catheter deflectable distal tip includes:
  unlocking the actuator by movement of the actuator and the carriage from the first location;
  moving the actuator, the carriage and a retainer from the first location to the second location and correspondingly deflecting the catheter deflectable distal tip into the desired orientation with a flexible element attached between the actuator and the catheter deflectable distal tip, flexible element is attached to the retainer, and the retainer is movably coupled with the carriage, wherein:
    proximal movement of the actuator loads the flexible element in tension and pulls the deflectable distal tip in a first direction, and
    distal movement of the actuator loads the flexible element in compression and transmits a pushing force to the deflectable distal tip, and the transmitted pushing force deflects the deflectable distal tip in a second opposed direction; and
  locking the actuator at the second location by releasing the actuator at the second location, and when locked the deflectable distal tip is held in the desired orientation, wherein locking and unlocking includes holding the retainer and the flexible element laterally static relative to the handle.

10. The method of claim 9, wherein unlocking the actuator includes depressing the actuator.

11. The method of claim 9, wherein unlocking the actuator includes disengaging the actuator from a first brake portion in the handle, the actuator including a second brake portion sized and shaped to engage with the first brake portion.

12. The method of claim 10, wherein locking the actuator includes biasing the second brake portion of the actuator into engagement with the first brake portion.

13. The method of claim 9, wherein unlocking the actuator includes overcoming an opposing bias from a biasing member applied to the actuator.

14. The method of claim 9, wherein:
  unlocking and locking of the actuator moves the carriage laterally relative to the retainer, the flexible element and the direction of proximal and distal movement of the actuator, and
  proximal and distal movement of the actuator moves the carriage together with the retainer.

15. A catheter comprising:
  a catheter body extending from a catheter proximal portion to a catheter deflectable distal tip;
  a handle fixed to the catheter proximal portion;
  an actuator slidably coupled with the handle, the actuator is engaged with a carriage and the carriage is movably coupled with a retainer, the actuator is coupled to a push/pull wire through attachment of the push/pull wire to the retainer, the push/pull wire is anchored in the deflectable distal tip, the actuator is movable proximally and distally, and the actuator is movable laterally from a locked position to an unlocked position; and
    wherein depression of the actuator laterally moves the actuator and the carriage from the locked position to the unlocked position where the actuator is movable proximally and distally, and release of the actuator laterally moves the actuator from the unlocked position to the locked position where the actuator is restrained from proximal and distal movement, wherein the retainer and the push/pull wire are laterally static during depression and release relative to the handle, and
    movement of the push/pull wire proximally tensions the push/pull wire and pulls the deflectable distal tip in a first direction, and movement of the push/pull wire distally compresses the push/pull wire and transmits a pushing force to the deflectable distal tip, and the pushing force deflects the deflectable distal tip in a second opposed direction.

16. The catheter of claim 15, wherein the catheter handle includes a first brake portion, and the actuator includes a second brake portion sized and shaped to engage with the first brake portion and lock the actuator in place against proximal and distal movement.

17. The catheter of claim 16 further comprising a biasing element engaged with the actuator, and the biasing element biases the second brake portion of the actuator into engagement with the first brake portion.

18. The catheter of claim 16, wherein the first brake portion is engaged along a portion of the catheter body within the handle.

19. The catheter of claim 15, wherein:
  depressing and releasing of the actuator moves the carriage laterally relative to the retainer, the push/pull wire and the direction of proximal and distal movement of the actuator, and
  proximal and distal movement of the actuator moves the carriage together with the retainer and the push/pull wire.

20. The catheter of claim 19, wherein the actuator, including the retainer and the carriage, extends around the catheter body.

21. The catheter of claim 15 further comprising a flexible element guide extending outside of a catheter body, the flexible element guide is slidably engaged around the push/pull wire and extends from the actuator to the catheter body.

* * * * *